US012788218B2

(12) United States Patent
Foged et al.

(10) Patent No.: US 12,788,218 B2
(45) Date of Patent: Nov. 10, 2026

(54) INTRAORAL SCANNING SYSTEM USING MAGNETIC INDUCTION

(71) Applicant: 3SHAPE A/S, Copenhagen (DK)

(72) Inventors: Morten Vendelbo Foged, Copenhagen (DK); Christoph Vannahme, Holte (DK); Michael Pedersen, Allerød (DK); Søren Greve Jensen, Copenhagen (DK); Dmytro Chupryna Olegovych, Copenhagen (DK); Esben Rosenlund Hansen, Brønshøj (DK); Anders Robert Jellinggaard, Copenhagen (DK); Peter Dahl Ejby Jensen, Valby (DK); Kasper Krogh, Copenhagen (DK); Oliver Sundberg, Copenhagen (DK)

(73) Assignee: 3SHAPE A/S, Kobenhavn K (DK)

( * ) Notice: Subject to any disclaimer, the term of this patent is extended or adjusted under 35 U.S.C. 154(b) by 1042 days.

(21) Appl. No.: 17/433,670

(22) PCT Filed: Feb. 27, 2020

(86) PCT No.: PCT/EP2020/055149
§ 371 (c)(1),
(2) Date: Aug. 25, 2021

(87) PCT Pub. No.: WO2020/174048
PCT Pub. Date: Sep. 3, 2020

(65) Prior Publication Data

US 2022/0087519 A1 Mar. 24, 2022

(30) Foreign Application Priority Data

Feb. 27, 2019 (EP) .................................... 19159766
Mar. 11, 2019 (EP) .................................... 19161887

(51) Int. Cl.
*A61B 1/00* (2006.01)
*A61B 1/05* (2006.01)
(Continued)

(52) U.S. Cl.
CPC ...... *A61B 1/00101* (2013.01); *A61B 1/00016* (2013.01); *A61B 1/00029* (2013.01);
(Continued)

(58) Field of Classification Search
CPC ............ A61B 1/00101; A61B 1/00016; A61B 1/00029; A61B 1/00096; A61B 1/00105;
(Continued)

(56) References Cited

U.S. PATENT DOCUMENTS 5,931,669 A 8/1999 Fornoff et al.
6,239,868 B1 * 5/2001 Jung ......................... G01J 3/51 356/600

(Continued)

FOREIGN PATENT DOCUMENTS

CN 102548471 A 7/2012
CN 103329143 A 9/2013

(Continued)

OTHER PUBLICATIONS

Daniel Bobkin, see reference 28 in p. 28 of the Radio-frequency refenrece of Wikipedia (Year: 2008).*

(Continued)

*Primary Examiner* — Eric J Rosen
*Assistant Examiner* — Mirayda A Aponte
(74) *Attorney, Agent, or Firm* — Buchanan Ingersoll & Rooney PC

(57) ABSTRACT

Disclosed is an intra-oral scanning system including: a scanning device including at least a first magnetic induction coil; a replaceable scanning tip including at least a second magnetic induction coil; the scanning tip being removably (Continued)

connected to the scanning device; wherein the at least first and second magnetic induction coils are configured to provide power transfer and/or a communication signal between the scanning device and the scanning tip during operation of the scanning system.

28 Claims, 15 Drawing Sheets

(51) Int. Cl.

| | |
|---|---|
| ***A61B 1/06*** | (2006.01) |
| ***A61B 1/07*** | (2006.01) |
| ***A61B 1/24*** | (2006.01) |
| ***A61B 5/00*** | (2006.01) |
| ***A61C 9/00*** | (2006.01) |
| ***G06T 7/00*** | (2017.01) |
| ***G06T 7/40*** | (2017.01) |

(52) U.S. Cl.
CPC ...... *A61B 1/00096* (2013.01); *A61B 1/00105* (2013.01); *A61B 1/00172* (2013.01); *A61B 1/05* (2013.01); *A61B 1/0638* (2013.01); *A61B 1/07* (2013.01); *A61B 1/24* (2013.01); *A61B 5/0062* (2013.01); *A61B 5/0088* (2013.01); *A61C 9/0053* (2013.01); *G06T 7/0012* (2013.01); *G06T 7/40* (2013.01); *A61B 1/0008* (2013.01); *G06T 2207/30036* (2013.01)

(58) Field of Classification Search
CPC ..... A61B 1/00172; A61B 1/05; A61B 1/0638; A61B 1/07; A61B 1/24; A61B 1/0008; A61B 5/0062; A61B 5/0088; A61C 9/0053; G06T 7/0012; G06T 7/40; G06T 2207/30036
USPC .............................................. 433/29; 269/287
See application file for complete search history.

(56) References Cited

U.S. PATENT DOCUMENTS

| | | | | |
|---|---|---|---|---|
| 6,295,082 | B1 | 9/2001 | Dowdy et al. | |
| 6,398,549 | B1 | 6/2002 | Koivisto et al. | |
| 7,129,472 | B1 | 10/2006 | Okawa et al. | |
| 9,036,140 | B2 | 5/2015 | Mihajlovic et al. | |
| 9,522,054 | B2 | 12/2016 | Kim et al. | |
| 9,962,244 | B2 | 5/2018 | Esbech et al. | |
| 10,736,718 | B2 | 8/2020 | Esbech et al. | |
| 2006/0022800 | A1 * | 2/2006 | Krishna | G06K 7/0008 340/10.2 |
| 2014/0022356 | A1 | 1/2014 | Fisker et al. | |
| 2014/0055586 | A1 | 2/2014 | Pasini et al. | |
| 2014/0248576 | A1 | 9/2014 | Tchouprakov et al. | |
| 2016/0295085 | A1 | 10/2016 | Aoyama | |
| 2017/0202483 | A1 | 7/2017 | Sorimoto et al. | |
| 2018/0028063 | A1 | 2/2018 | Elbaz et al. | |
| 2020/0330195 | A1 | 10/2020 | Moalem | |
| 2022/0133447 | A1 | 5/2022 | Hansen et al. | |
| 2022/0151756 | A1 | 5/2022 | Pesach et al. | |

FOREIGN PATENT DOCUMENTS

| | | | | |
|---|---|---|---|---|
| CN | 104812291 | A | 7/2015 | |
| CN | 105263437 | A | 1/2016 | |
| CN | 107661159 | A * | 2/2018 | A61B 1/24 |
| CN | 109069350 | A | 12/2018 | |
| EP | 1350459 | A1 | 8/2003 | |
| EP | 2923630 | A1 | 9/2015 | |
| EP | 3064897 | A1 | 9/2016 | |
| EP | 3121558 | A1 | 1/2017 | |
| JP | 2016013272 | A | 1/2016 | |
| JP | 2018149187 | A | 9/2018 | |
| KR | 101662566 | B1 | 10/2016 | |
| KR | 20180126166 | A | 11/2018 | |
| WO | 2006041459 | A1 | 4/2006 | |
| WO | 2008061225 | A2 | 5/2008 | |
| WO | WO-2011140664 | A2 * | 11/2011 | A61B 1/00177 |
| WO | 2012099977 | A2 | 7/2012 | |
| WO | 2016084066 | A1 | 2/2016 | |
| WO | 2018005009 | A1 | 1/2018 | |
| WO | 2018022940 | A1 | 2/2018 | |
| WO | 2018073824 | A1 | 4/2018 | |
| WO | WO-2018168681 | A1 * | 9/2018 | A61B 5/0088 |
| WO | 2018177795 | A1 | 10/2018 | |
| WO | 2020053136 | A1 | 3/2020 | |

OTHER PUBLICATIONS

Benamara et al., A Twisted Loop Antenna to Enhance HF RFID Detection for Different Tag Positioning, (Year: 2015).*
Second Office Action issued on Apr. 25, 2024, by the Chinese Patent Office in corresponding Chinese Patent Application No. 202080031478.4, and an English Translation of the Office Action. (18 pages).
Second Office Action issued on Jun. 18, 2024, by the Chinese Patent Office in corresponding Chinese Patent Application No. 202080031491.X, and an English Translation of the Office Action. (20 pages).
Office Action issued on Jun. 21, 2024, by the U.S. Patent and Trademark Office in U.S. Appl. No. 17/434,064. (43 pages).
Office Action (Decision of Rejection) issued on Jul. 22, 2024, by the Chinese Patent Office in corresponding Chinese Patent Application No. 202080031478.4, and an English Translation of the Office Action. (22 pages).
Office Action issued on Nov. 21, 2024, by the Korean Patent Office in corresponding Korean Patent Application No. 10-2021-7030503, and an English Translation of the Office Action. (15 pages).
Office Action (Final Rejection) issued on Dec. 16, 2024, by the U.S. Patent and Trademark Office in co-pending U.S. Appl. No. 17/434,064. (23 pages).
International Search Report (PCT/ISA/210) and Written Opinion (PCT/ISA/237) mailed on May 28, 2020, by the Japan Patent Office as the International Searching Authority for International Application No. PCT/EP2020/055149. (25 pages).
Megdouda et al., "A Twisted Loop Antenna to Enhance HF RFID Detection for Different Tag Positioning", 2016 10th European Conference on Antennas and Propagation (EUCAP), European Association of Antennas and Propagation, Apr. 10, 2016, pp. 1-5, XP032906813.
First Office Action issued on Dec. 4, 2023, by the Chinese Patent Office in corresponding Chinese Patent Application No. 202080031478.4, and an English Translation of the Office Action. (21 pages).
First Office Action issued on Nov. 30, 2023, by the Chinese Patent Office in corresponding Chinese Patent Application No. 202080031491.X, and an English Translation of the Office Action. (20 pages).
3SHAPE, Trios Basic Workflow, Apr. 9, 2014, 1 page.
U.S. Appl. No. 17/434,064, filed Aug. 26, 2021, Esben Rosenlund Hansen.
Office Action issued on Mar. 11, 2026, by the U.S. Patent and Trademark Office in co-pending U.S. Appl. No. 17/434,064. (21 pages).
The extended European Search Report issued on Mar. 15, 2024, by the European Patent Office in corresponding European Application No. 24152029.5. (9 pages).
Office Action issued on Oct. 10, 2025, by the U.S. Patent and Trademark Office in co-pending U.S. Appl. No. 17/434,064. (22 pages).
Office Action issued on Apr. 23, 2025, by the U.S. Patent and Trademark Office in co-pending U.S. Appl. No. 17/434,064. (29 pages).

* cited by examiner

INTRAORAL SCANNING SYSTEM USING MAGNETIC INDUCTION

TECHNICAL FIELD

This invention generally relates to a scanning system for intraoral scanning of teeth. More specifically, the present disclosure relates to the construction and function of scanner tips for intraoral scanner devices using infrared transillumination and white light, and to scanning systems using magnetic induction for power transfer and/or communication.

BACKGROUND

Scanner devices for intraoral scanning of teeth are well known in the field of scanning.

In intraoral scanning of teeth and gingiva, data is normally acquired from the intraoral cavity with a scanner device providing white light, or a combination of one or more distinct wavelengths of light, to illuminate the intraoral cavity. The scanner device typically has one or more image sensors for acquiring images or data from the scanning process.

WO2018/022940 describes an intraoral scanner using infrared light in the range of 700 to 1090 nm. It describes how non-ionizing methods of imaging and/or detecting internal structures may be used, such as taking images using a penetrating wavelength to view structures within the teeth by illuminating them using one or more penetrative spectral ranges (wavelengths), including using trans-illumination (e.g., illuminating from one side and capturing light from the opposite side after passing through the object), and/or small-angle penetration imaging (e.g., reflective imaging, capturing light that has been reflected/scattered from internal structures when illuminating with a penetrating wavelength).

However, the design of a scanner device capable of both using visible light and infrared light wavelengths for capturing information about the scanned object, may be very complicated.

It therefore remains a desire in the field of intraoral scanning to provide a device with a simpler and cheaper design of a scanner device capable of employing light in both visible and infrared wavelengths.

SUMMARY

In one aspect, disclosed is an intra-oral scanning system comprising:

- a scanning device comprising at least a first magnetic induction coil;
- a replaceable scanning tip comprising at least a second magnetic induction coil;
- the scanning tip being removably connected to the scanning device;
- wherein the at least first and second magnetic induction coils are configured to provide power transfer and/or a communication signal between the scanning device and the scanning tip during operation of the scanning system.

By employing magnetic induction coils for power transfer and/or communication between the scanner device and the scanning tip, there is no need for electrical contacts. This makes it possible to hermetically seal both the scanner and scanning tip and makes it easier to clean surfaces that can now be made flush, reducing the challenges of cleaning and disinfection.

In some embodiments, the power transfer from the scanning device to the scanning tip comprises supplying an alternating voltage or electrical current in the first magnetic induction coil, thereby inducing an electrical current in the second magnetic induction coil.

In some embodiments, providing the communication signal between the scanning device and the scanning tip comprises providing a frequency, phase or amplitude modulated alternating voltage or current to either the first or second coil, thereby inducing a modulated signal in the other of the first or second coil, wherein the modulated signal comprises the communication transfer from the scanning device to the scanning tip or from the scanner tip to the scanning device.

In this way, it is possible to send communication back and forth between the scanning device and the scanning tip.

In some embodiments, the scanning system is configured to demodulate the modulated signal.

In some embodiments, the communication signal is placed in a different frequency band than the power transfer signal.

This reduces the possible interference between the power transfer and communication signals.

In some embodiments, the scanning device further comprises a third magnetic induction coil; the scanner tip further comprises a fourth magnetic induction coil; and the first and second magnetic induction coils are configured to provide the power transfer, and the third and fourth magnetic induction coils are configured to provide the communication transfer.

In this way, there will be dedicated induction coils for power transfer and dedicated induction coils for communication.

In some embodiments, the third and/or fourth communication transfer induction coils are twisted 180 degrees around a symmetrical centre, the third and fourth induction coils thereby comprising two halves in the shape of a figure of 8.

This configuration of the coils has the effect that placing the communications coil in a uniform, alternating field such as the above mentioned power transmission field, would cause the induced in signal in the communications coil to cancel out due to the opposite polarity of the induced current localized to each of the twisted coils.

In some embodiments, the scanning-tip further comprises:

- an optical element located at the distal end of the scanning-tip with a reflective surface inside the scanning-tip such that when the optical element receives light from a white light source located in the scanning device, the scanning tip provides white light to the teeth, wherein the optical element is configured for receiving the white light as back-reflected from the teeth, such that when the optical element receives the white light from teeth, the scanning-tip provides the white light to a first image sensor in the scanning device; and
- an infrared light source configured to emit infrared light, the infrared light source residing in or on the replaceable scanning-tip, whereby the scanning tip provides the infrared light to the teeth.

In this configuration, it is possible to use the same scanning device for both optical and infrared imaging.

In another aspect, disclosed herein is an intra-oral scanning system comprising:

- a scanning device;

- a semi-replaceable scanning tip comprising at least a first magnetic induction coil;
- an infrared adapter configured to replaceably attach to the scanning tip, the infrared adaptor comprising at least a second magnetic induction coil and at least one infrared light source;
- a disposable or reusable hygiene sheath disposed between the scanning tip and the infrared adapter;
- wherein the at least first and second magnetic induction coils are configured to provide power transfer and/or a communication signal between the scanning device and the scanning tip during operation of the scanning system.

By employing magnetic induction coils for power transfer and/or communication between the scanner device and the scanning tip, there is no need for electrical contacts. This makes it possible to hermetically seal both the scanner and scanning tip and makes it easier to clean surfaces that can now be made flush, reducing the challenges of cleaning and disinfection. Furthermore, the disposable or reusable hygiene sheath can be changed between each patient, thereby reducing the risk of contamination between patients. The infrared adapter may also be disposable for one-time use, so that the part going into the patient's mouth can be discarded after use.

The infrared adapter may also be autoclavable enabling re-use. Since the infrared adapter in this embodiment does not include any electronics, it is able to withstand a more rigorous cleaning between uses.

In some embodiments, the infrared adapter is configured to attach to the scanning tip by snapping and/or sliding onto the scanning tip.

This allows for the easy attachment and removal of the infrared adapter before and after use.

In another aspect there is disclosed a replaceable scanning-tip for a scanning device, the scanning-tip being configured for intra-oral scanning of teeth, the scanning-tip comprising:

- an optical element located at the distal end of the scanning-tip with a reflective surface inside the scanning-tip such that when the optical element receives light from a white light source located in the scanning device, the scanning tip provides white light to the teeth, wherein the optical element is configured for receiving the white light as back-reflected from the teeth, such that when the optical element receives the white light from teeth, the scanning-tip provides the white light to a first image sensor in the scanning device; and
- an infrared light source configured to emit infrared light, the infrared light source residing in or on the replaceable scanning-tip, whereby the scanning tip provides the infrared light to the teeth.

Accordingly, since the scanner tip is replaceable, the design of the scanner device can be made more flexible, with a simpler design and a cheaper manufacturing process.

In some embodiments, the replaceable scanning tip further comprises a replaceable infrared adapter, the infrared adapter comprising one or more light guides for guiding the infrared light from the scanning tip to the teeth and/or gingiva.

The infrared adapter in these embodiments may be manufactured without any electronics and will therefore be cheaper and easier to manufacture.

In some embodiments, the light guides of the infrared adapter comprise a core and a cladding material, wherein the reflective index of the core is higher than the reflective index of the cladding, such that the infrared light experiences total internal reflection when passing through the one or more light guides.

By having a core with higher reflective index than the cladding, the loss of infrared light is reduced.

In some embodiments, the light guides of the infrared adapter comprise one or more mirrors such that the infrared light experiences total internal reflection when passing through the one or more light guides By having mirrors for reflecting the light, the loss of light from bends in the light guide can be reduced.

In some embodiments, the scanning tip and/or the infrared adapter further comprises one or more windows between the infrared light source and the one or more light guides.

Having windows between the infrared light source and the light guides, the coupling of the light from the light source to the light guide is increased.

In some embodiments, the one or more windows are made from polymers and/or glass.

In some embodiments, the scanning tip comprises a first window placed next to the infrared light source, and the infrared adapter comprises a second window, the first and second windows configured to couple the infrared light from the infrared light source to the one or more light guides.

This allows the separation of the parts between the infrared light source and the light guide.

In some embodiments, air gaps between the infrared adapter and the first window are filled with a transparent cladding material.

This allows the reduction of the difference in the effective refractive index between the infrared light source and the light guides.

In some embodiments, the infrared adapter is configured to attach to the scanning tip by snapping and/or sliding onto the scanning tip.

This allows for the easy attachment and removal of the infrared adapter before and after use.

In some embodiments, the optical element is further configured for receiving the infrared light as back-reflected from the teeth, such that when the optical element receives infrared light from the teeth, the scanning-tip provides infrared light to a second image sensor.

In these embodiments, two image sensors of the optical system may be chosen to have different sensitivities at different wavelengths of light. For example, the first sensor may be more sensitive to light with wavelengths in the visible spectrum, for example between 400 to 700 nm, while the second sensor may be more sensitive to infrared light with wavelengths between 750 nm to 1000 nm.

In some embodiments comprising two image sensors, the second image sensor is identical to the first image sensor. This allows for a simpler and cheaper construction of the scanning-tip.

In some embodiments, the optical element is configured to reflect the white light such that it passes to a first set of pixels on the first image sensor, and wherein the optical element is configured to reflect the infrared light such that it passes to a second set of pixels on the first image sensor. In this way it is possible to have a single sensor, divided into pixel groups being used for the detection of the white light and infrared light respectively.

In one embodiment, the optical element is a mirror.

In another embodiment, the optical element comprises a glass plate. In some embodiments, the optical element comprises an optical coating. An optical coating is one or more layers of material that is deposited on the optical element, for example a glass plate, such as forming a mirror.

The optical coating alters the way the wavelengths of the light are reflected and/or transmitted on or in the optical element.

In a preferred embodiment, the optical coating is a dielectric coating. A dielectric coating comprises materials with different refractive index as made from a plurality of layers, wherein the thickness of the plurality of layers may be selected according to a specific wavelength reflection and/or transmission. More specifically, by the selection of the exact composition, thickness, and/or number of the plurality of layers, it is possible to tailor the reflectivity and/or transmittivity of the coating to produce a desired characteristic. In one embodiment, the dielectric coating is selected such that each of the layers are less than 300 nm, such as less than 200 nm, preferably around 100 nm.

An advantage of having the optical element to comprise a dielectric coating, particularly where the optical element resides in the scanning-tip, is that the desired characteristic (in the embodiment where the scanning-tip is replaceable) may be replaced by another scanning-tip having another desired characteristic. The dielectric coating as placed on or integrated in the optical element, is this an alternative solution to placing dielectric coating on an optical element inside the scanning device, for example on a beam splitter or on top of the imaging sensor. This alternative solution provides thus for a more flexible scanning device where the desired characteristic can be replaced according to a specific scanning mode. Another advantage of having the optical element to comprise a dielectric coating is that the scanning device without the scanning-tip (replaceable or not) can be made in an efficient manner where dielectric coating needs not to be applied to surface inside the scanning device. This may therefore allow for a more cost-effective production of the scanning device.

In a most preferred embodiment, the dielectric coating is selected such that the refractive indices and thicknesses of the plurality of layers provide a relative phase shift between S-polarized light and P-polarized light that is around 0 degrees or 180 degrees. The tolerance of the phase shift (around the 0 or 180 degrees) may in some embodiments be less than plus or minus 15 degrees, such as plus or minus 10 degrees or such as plus or minus 5 degrees. In some embodiments, the phase shift is selected for light in the range between 400-600 nm, such as between 500-575 nm. In some embodiments, the phase shift is selected for light in the range between 400-600 nm, such as between 490-585 nm. For example, two different ranges may be selected for two different layers. An advantage of having about 0 degrees change in the polarization between S-polarized light and P-polarized light is that the polarization does not change for a selected wavelength range. In this manner, specular reflection from teeth may for example be enhanced.

In another preferred embodiment, the dielectric coating is selected such that the refractive indices and thicknesses of the plurality of layers provide a reflection of more than 90%, such as more than 95%, for both S-polarized light and P-polarized light. In yet another preferred embodiment, the dielectric coating is selected such that the refractive indices and thicknesses of the plurality of layers provide a reflection of more than 80% for non-polarized light. In some embodiments, the reflection is selected for light with wavelengths in the visible domain, i.e. with wavelengths in the range between 400-600 nm, such as between 500-575 nm, such as between 490-585 nm. For example, two different ranges may be selected for two different layers. In other and/or additional embodiments, the reflection is selected for light in the infrared domain, i.e. with wavelengths in the range between 700-1000 nm, such as between 800-900 nm, such as between 820-880 nm.

The polarization and/or reflection is in most preferred embodiments selected for an angle of incidence of between 30-60 degrees, such as between 40-50 degrees, such as around 45 degrees. This may provide that light may be guided from the scanning device and into an intra-oral cavity, for example without changing the polarization between S-polarized light and P-polarized light, and/or for example with both high reflection (more than 80%) for both light in the visible domain and in the infrared domain.

In some embodiments, the replaceable scanning-tip comprises one or more light blockers at the distal end of the scanning-tip, said light blockers being configured to block direct and or indirect stray light. Minimizing the amount of stray light by the utilization of light blockers, ensures a superior image quality, since stray light generally lowers the information available in captured images by blurring out, overexposing and/or causing glare in parts of the image captured.

In some embodiments, the replaceable scanning-tip comprises a plurality of infrared light sources located at or near the above-mentioned light blockers. In a preferred embodiment, three IR LEDs are placed on each side of the scanning-tip. These three IR LEDs may be electrically connected in series. In some instances, a dedicated connection from the scanning device provide power to all six IR LEDs. In order to evenly split the electrical current between the two chains of IR LEDs, a current mirror may be utilized. This helps ensure an even illumination of infrared light. The scanning device may further contain electrical circuitry, which can measure the voltage and current supplied to the IR LEDs to determine and control the desired amount of infra light. As a safety measure a temperature sensor may be placed adjacent to each chain of IR LEDs. If the temperature rises above normal operating range, the temperature sensor disconnects one or more, preferably all six IR LEDs from the power supply, by turning off a transistor connected in series with the IR LEDs. This prevents the surface of the scanning-tip from becoming too hot, which could cause discomfort or harm to the patient. It also prevents excessive infrared light, because if too much power is supplied to the IR LEDs, they will become too hot for comfort and/or safety of the patient.

In some embodiments, the light blockers comprise an integrated shape on the inside of distal end of the scanning tip, wherein the integrated shape is configured to aid the user to position the device correctly with respect to the teeth and the gingiva. The shape of the integrated part may for example be in the form of a long protrusion, positioned above the IR LEDs. This shape allows the user to arbitrarily position the device in any position with the teeth in scope, and/or with the correct placement of the tip with respect to the gingiva, The integrated part may alternatively be in the form of a pyramidal shape, which allows the user to position the scanning tip in such a way, that the pyramid shaped protrusion is placed in the gap between the teeth. This ensures that the tip is correctly placed with respect to the teeth, as well as the gingiva.

In one embodiment, the scanning-tip further comprises a recognition-interface linked to an integrated memory located in the scanning-tip, the recognition-interface being configured to be read by a recognition-component located on the scanning device when the scanning-tip is mounted on the scanning device.

In a second embodiment, the scanning-tip comprises a plurality of connectors, such as pins. For example, the recognition-interface may be part of the plurality of connectors. In one embodiment, the integrated memory may store a serial number and/or additional data. The integrated memory may be an EEPROM.

In some embodiments, the recognition-interface is in the form of at least an I2C interface. An I2C interface provides an SCL signal (I2C serial interface clock signal) and an SDA signal (I2C serial interface data signal). Two connectors may for example provide the I2C signals.

In another embodiment, the plurality of connectors is in the form of a first plurality of connectors and a second plurality of connectors, wherein the plurality of connectors are located at the proximal end of the scanning-tip. The first plurality of connectors may be located at an upper location of the proximal end, and the second plurality of the connector may be located at a lower location end of the proximal end. The first plurality of pins and the second plurality of pins may be identical. This may allow the scanning-tip to be mounted in two positions to the scanning-device.

In a preferred embodiment, the plurality of connectors forms six pins. For example, in addition to two I2C connectors in the form of pins, there may be a common ground pin, and three voltage pins, such as a constant voltage pin, a first variable voltage supply, and a second variable voltage supply. The constant voltage pin may provide voltage to a digital logic circuit in the scanning-tip. The first variable voltage pin may provide voltage heating the optical element in the scanning-tip. The second variable voltage pin may provide voltage to an infrared light source located on or in the scanning-tip.

In another preferred embodiment, the plurality of connectors forms twelve pins. For example, the six pins as described above, may be located at an upper location of the proximal end, and six other but identical pins may be located at a lower location of the proximal end.

In a most preferred embodiment, the plurality of connectors in the form of a first plurality of connectors and in the form of a second plurality of connectors are of the same type but located such that the first plurality of connectors is located along one arch and the second plurality of connectors is located along another arch. This may allow the scanning-tip to be rotated from one position to another position.

In another preferred embodiment, the plurality of connectors in the form of a first plurality of connectors and in the form of a second plurality of connectors are of the same type but located such that when the scanning-tip is rotated from one position to another position, for example rotated by 180 degrees, the first plurality of connector types are different from the second plurality of connector types. This may also allow the scanning-tip to be rotated from one position to another position but may further allow the scanning device to identify the difference, and thereby identify whether the scanning-tip points upwards or downwards.

In some embodiments, the replaceable scanning-tip comprises a printed circuit board integrated in the scanning-tip, the printed circuit board being (PCB) configured to provide electricity from the scanning device to the infrared light source. The PCB may comprise two L shaped arms made of flexible PCB.

In some embodiments, the white light is defined by light comprising one or more wavelengths in the range between 400 nm to 700 nm. An advantage of using wavelengths in this range, is that it allows for the capture of colour information that realistically corresponds to real-life colour information.

In some embodiments, the replaceable scanning-tip used infrared light, defined by light comprising one or more wavelengths in the range between 750 nm to 1000 nm. Using infrared light in this wavelength range allows for the light to propagate through the gingiva and tooth material to illuminate the tooth from the inside.

In some embodiments, the replaceable scanning-tip comprises a tubular member comprising a distal end comprising a first optical opening configured to transmit the at least white light to the teeth, and a proximal end comprising a second optical opening configured to transmit the at least white light from the scanning device to the first optical opening, and the proximal end further comprising a mounting interface configured to mount the scanning-tip to the scanning device.

In some embodiments, the replaceable scanning-tip comprises a shell made up of at least two distinct parts. The first part may be referred to as a hard part, made from a plastic such as polysulfone, PSU 1700 or similar plastics. The second part may be referred to as a soft part, made from a biocompatible material, such as medico silicone rubber shore 60*a* or 70*a*. Other similar materials may be utilized for the hard part and the soft part of the scanning tip.

In some embodiments, the LEDs are placed in a retracted position in the soft part. In these embodiments, the protruded part above the LEDs functions as an additional light blocker. The remaining three sides around the LEDs may be slanted to allow for maximum light output into the gingiva.

The front of the scanning tip serves as both a mechanical locking feature but also as a bumper that minimizes the patient feel in the event that the device hits the back of mouth and or gingiva.

The long flat concave area which runs underneath the tip serves both as an area for applying glue, but it also aids as a guard to ensure that the device does not feel unpleasant due to impact between teeth and the aggregate. Furthermore, there may be several channels running along the bottom section allowing easy alignment between the soft and the hard part when the two parts are glued together during assembly.

The silicone material which the soft part of the tip is made of feels nice and smooth, especially when it is wetted from saliva. This has the effect that the user feels less of the friction of the material in the mouth, for example on the teeth, gingiva, tongue or other soft tissue when the tip is being maneuvered into position.

According to an aspect, disclosed is a scanning system comprising:

the replaceable scanning-tip as described in any of the embodiments disclosed herein, and a scanner device configured to replaceably mount the replaceable scanning-tip.

By having a scanner device that can replaceably mount the scanning-tip, the scanner device will be more versatile. Other types of scanning-tips may be employed, and he replaceable scanning-tip may be changed for each new patient, and/or be autoclaveable. This allows for a more hygienic scanning system.

BRIEF DESCRIPTION OF THE DRAWINGS

The above and/or additional objects, features and advantages of the present invention, will be further described by the following illustrative and non-limiting detailed description of embodiments of the present invention, with reference to the appended drawing(s), wherein.

DETAILED DESCRIPTION

In the following description, reference is made to the accompanying figures, which show by way of illustration how the invention may be practiced.

Figure 1:
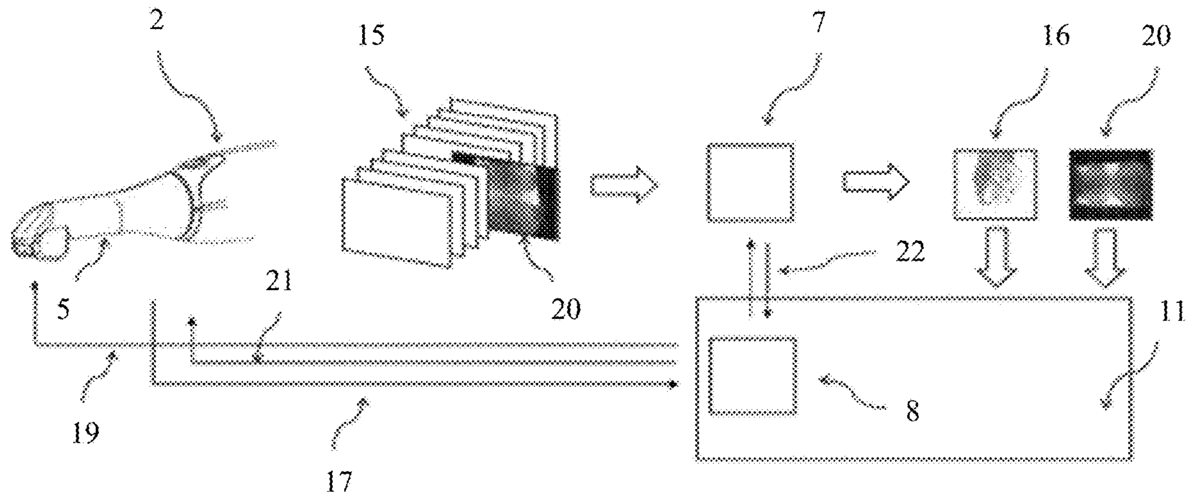
FIG. 1 shows a scanning system according to embodiments of the disclosure

FIG. 1 shows a scanning system according to an embodiment of this disclosure. In this example, the scanning system 1 is configured for performing intra-oral scanning of at least a portion of a tooth using at least infrared light.

Further, in this example, the scanning system 1, more particularly the processor 7, is configured to operate in a second processing-mode corresponding to scanning intra-orally with at least infrared light using a scanning-tip 5 therefor.

This second processing-mode is initiated by mounting the intra-oral tip 5 with a mirror in the distal end that covers the entire optical field-of-view and directs light from the scanner device 2 towards the object to be scanned. The intra-oral tip 5 is shown mounted. This tip is configured for being inserted into the mouth of a patient. Further, in one configuration of the scanning-device 2, the light is selected to trans-illuminate the object to be scanned.

When the scanning tip 5 is mounted to the scanner device 2, the scanner device 2 reads recognition data 17 in the form of an identification-number 17 of the tip 5 which is stored on an internal memory of the scanning tip 5. The identification-number is forwarded to the controller 8 located on the externally connected computer 11 Based on the scanner-tip identification-number 17, the controller 8 instructs the processor 7 on the scanner device 2 to process a continuous sequence of 2D-images 15 recorded with an infrared-light illumination on the object. To do this, the scanner device 2 is configured to illuminate the object with infrared light into the object, for example into a tooth, and the surrounding gingiva. The scanning tip 5 is configured such that the red light propagates through the gum and tooth material to illuminate the tooth from the inside. The infrared light illumination is controlled by the controller 8 and based on the scanner-tip identification-number 17. In other words, when the controller 8 receives the scanner-tip identification-number 17, the controller 8 additionally instructs the scanner device 2 to emit the infrared light. Further, the controller 8 additionally instructs the scanner device 2 to emit the white light.

In this manner, a regular sequence of images 15 is recorded with the white-light illumination. However, at a specific point in time, the white light recording is momentarily interrupted to record a single image 20 with infrared illumination. The interruption is based on scan data feedback 21 between the controller 8 and the scanner device 2, the feedback 21 being also based on data 22 from the processor 7. The data 22 from the processor 7 may for example be a 2D image index-number of the infrared image 19. The index-number may be dynamically determined for each image in the sequence of images 15.

Further, when in the second processing-mode, the processor 7 processes the white light images to derive both data for 3D geometry and data for texture for the surface. Further, the processor 7 processes the single infrared light image to derive data for texture of the internal structure of the object. Finally, the processor correlates data for the texture of the internal structure of the object to the data for the 3D geometry.

In this example, the scanning application correlates the infrared image 15 to a corresponding position on the 3D-model 13.

Figure 2:
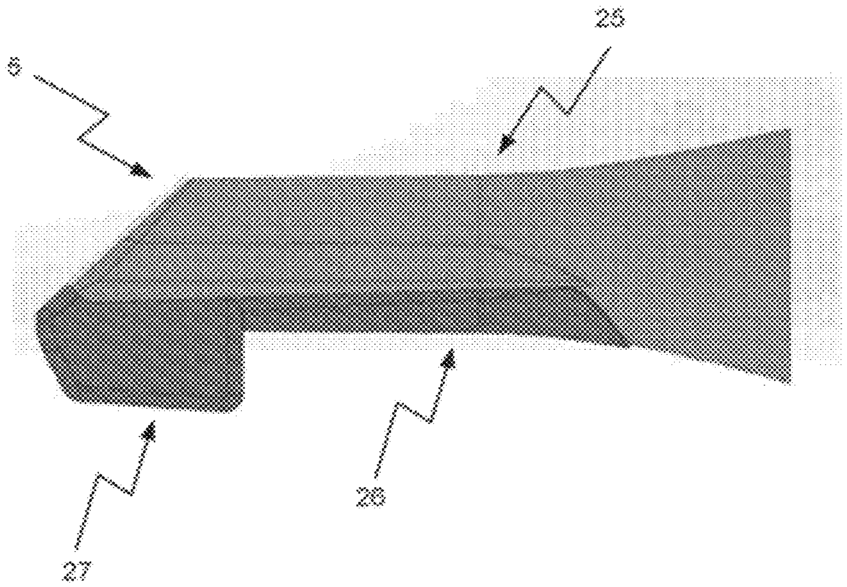
FIG. 2 shows a side view of a scanning tip according to embodiments of the disclosure

FIG. 2 shows a side view of the scanner tip 5 according to an embodiment of this disclosure. The scanning tip 5 may be either integrated in a scanning device, or preferably be a replaceable scanning-tip for a scanning device. The scanning tip 5 comprises a shell made up of at least two distinct parts, hereafter referred to as a hard part 25 and a soft part 26. The lower inclination 27 of the soft part 26 ensures that the aggregate does not collide with the front teeth when the aggregate is positioned over the largest teeth in scope. The angling of this part of the tip allows for the tip to be moved into the mouth at an angle to allow for the best maneuverability and functionality. The light blocker protrusions/not visible in this view) may also follow this same inclination.

The front inclination 28 of the soft part ensures that the device can be moved all the way into the mouth cavity and inspect the interproximal area between the two rear molars.

Figure 3:
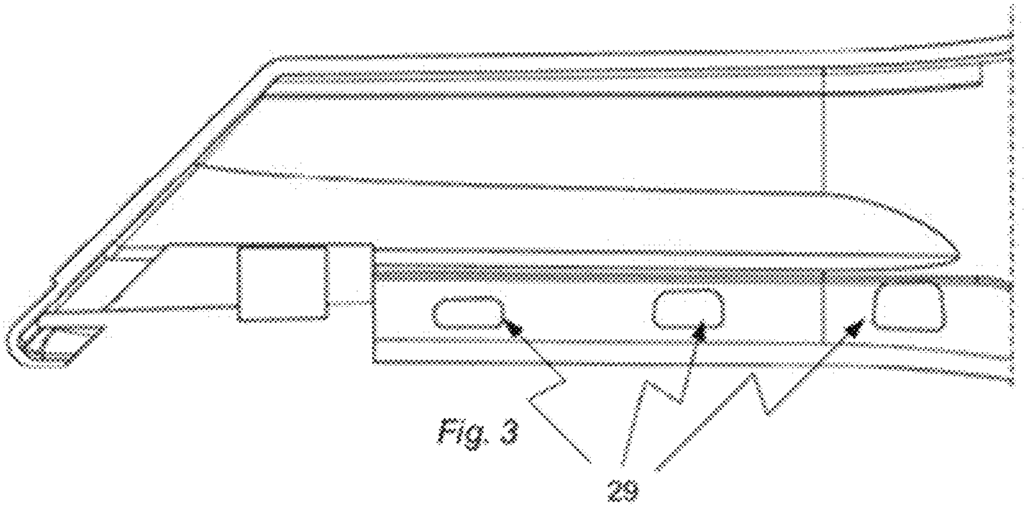
FIG. 3 shows a side view of a first, hard part of the shell of the scanning-tip according to embodiments of the disclosure

FIG. 3 shows a side view of the hard part 25 of the shell of the scanning tip 5 according to embodiments of this disclosure.

Figure 4:
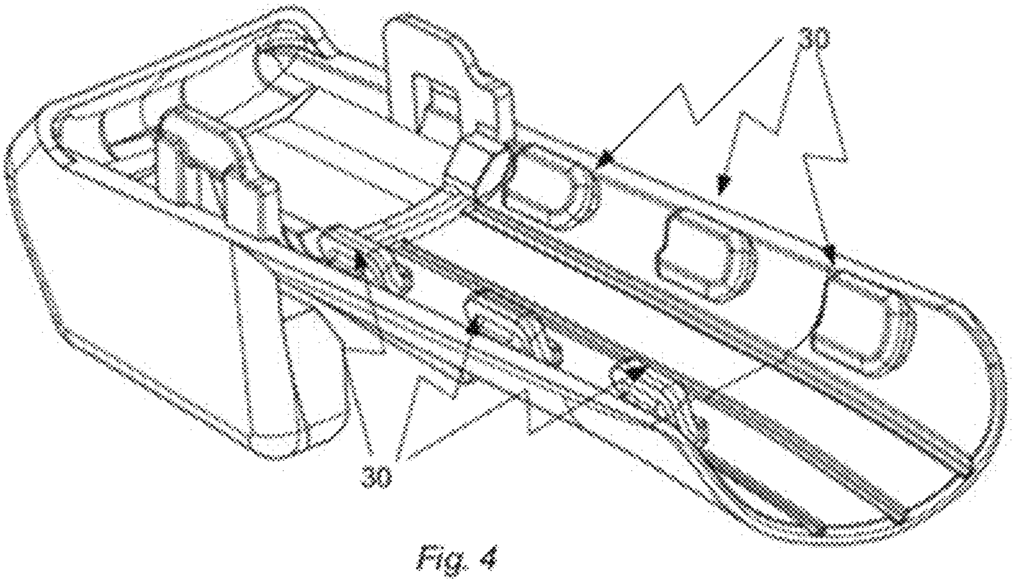
FIG. 4 shows a view of a second, soft part of the shell of the scanning-tip according to embodiments of the disclosure

FIG. 4 shows a view of the soft part 26 of the shell of the scanning tip 5 according to embodiments of this disclosure. The soft part of the shell comprises protrusions, here illustrated in the shape of mushroom heads 30, although other shapes may equivalently be used.

Figure 5:
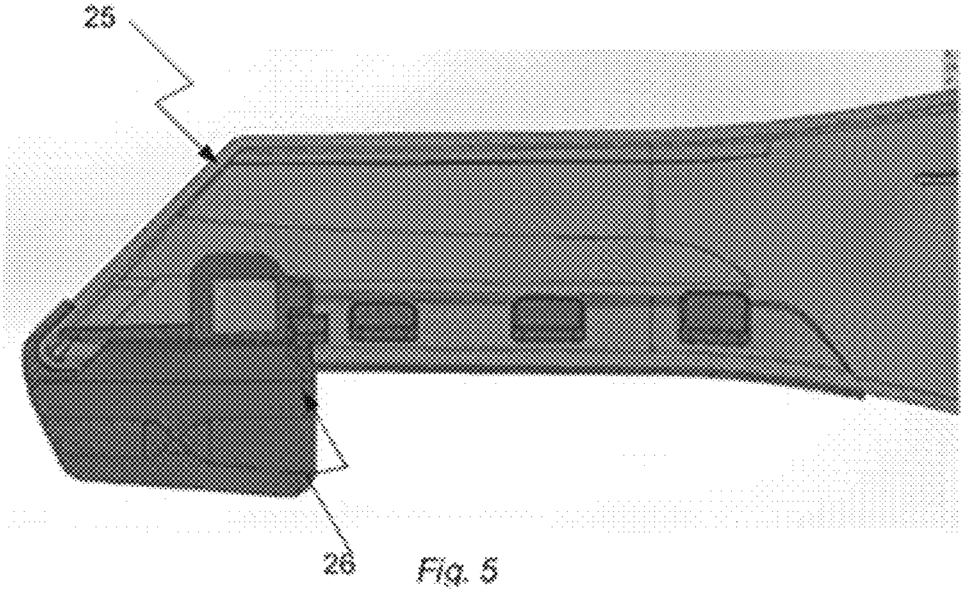
FIG. 5 shows a side view of the scanning-tip according to embodiments of the disclosure, showing the first and second part connected according to embodiments of the disclosure

FIG. 5 shows a side view of the shell of the scanning tip 5 according to embodiments of this disclosure, after the hard part 25 and the soft part 26 have been attached together. The interaction between the two parts incorporate several features in order to mechanically lock them together and to have surfaces that allow for enough gluing in order to hold them together. The mechanical locking connections are that the front 51 of the soft part 26 overlaps the hard part 25. The hard part has window openings 29, on the inside of which is located a feature or protrusion onto which the soft part 26 is mechanically snapped and fixed in place. A small protrusion or feature overlaps the corner of the window opening to position and mechanically hold the soft part in place. The back end of the soft part 26 may comprise one or more features, here illustrated shaped as mushroom heads 30 placed on each side around the vertical center plane. Although illustrated here as mushroom heads 30 placed symmetrically, other shapes and positioning may equivalently be used. The mushroom heads 30 mechanically snap into complementary holes or windows 29 comprised in the hard part 25. All of the above-mentioned features or protrusions also serve as surfaces for gluing the two parts together.

Figure 6A:
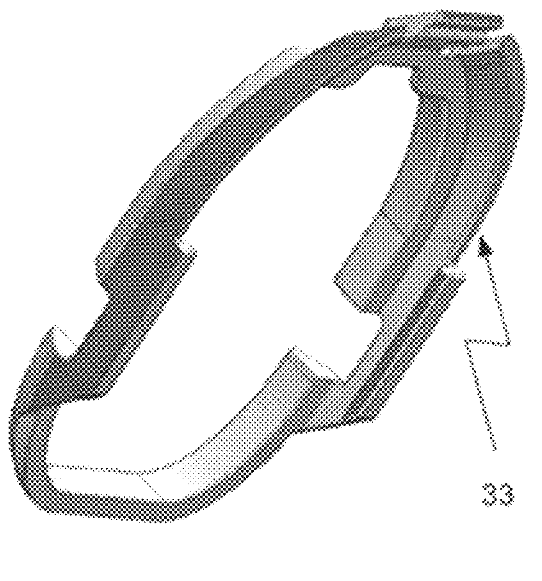
FIG. 6A shows a mirror frame for holding a mirror according to embodiments of this disclosure

FIG. 6A shows the frame 33 for holding the mirror in the tip according to embodiments of this disclosure. The frame for the mirror may comprise grooves incorporated in the sidewalls to allow for the PCB wings to extend out from the PCB heater element part and bend downward at the edge of the frame.

Figure 6B:
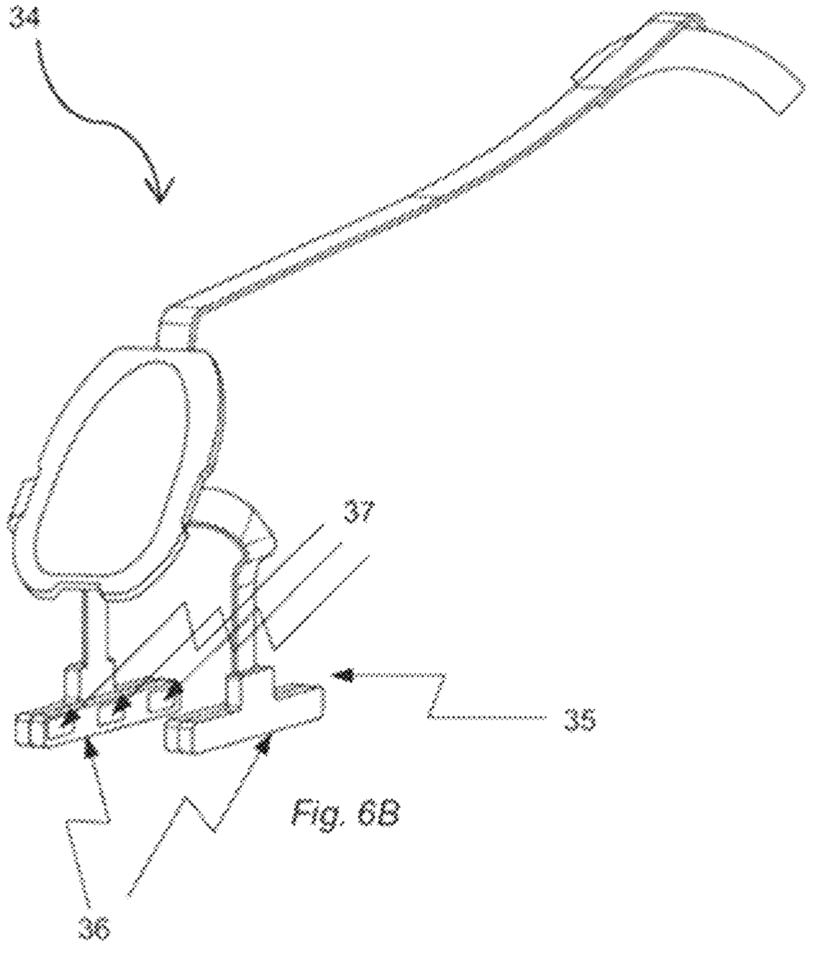
FIG. 6B shows a PCB part of the scanning-tip including mirror frame and arms for holding infrared LEDs according to embodiments of the disclosure

FIG. 6B shows a flexible printed circuit board (PCB) 34 of the scanning-tip according to embodiments of this disclosure. The flexible PCB 34 comprises two L shaped arms 35 made of flexible PCB. Each of these arms are symmetric and end in a rigid section 36. The rigid section 36 may be made from for example glass-reinforced epoxy laminate material such as FR4. Each arm of the PCB 34 comprises one or more IR LED's 37, here exemplified using 3 LEDs 37. The LEDs 37 point horizontally inwards towards the center plane. Furthermore, the PCB 34 may have an additional wire running along the spine connecting the LED's 37 to the 6th pin in the baronet/pogo pin connection between the scanning-tip and the scanner device.

Figure 7A:
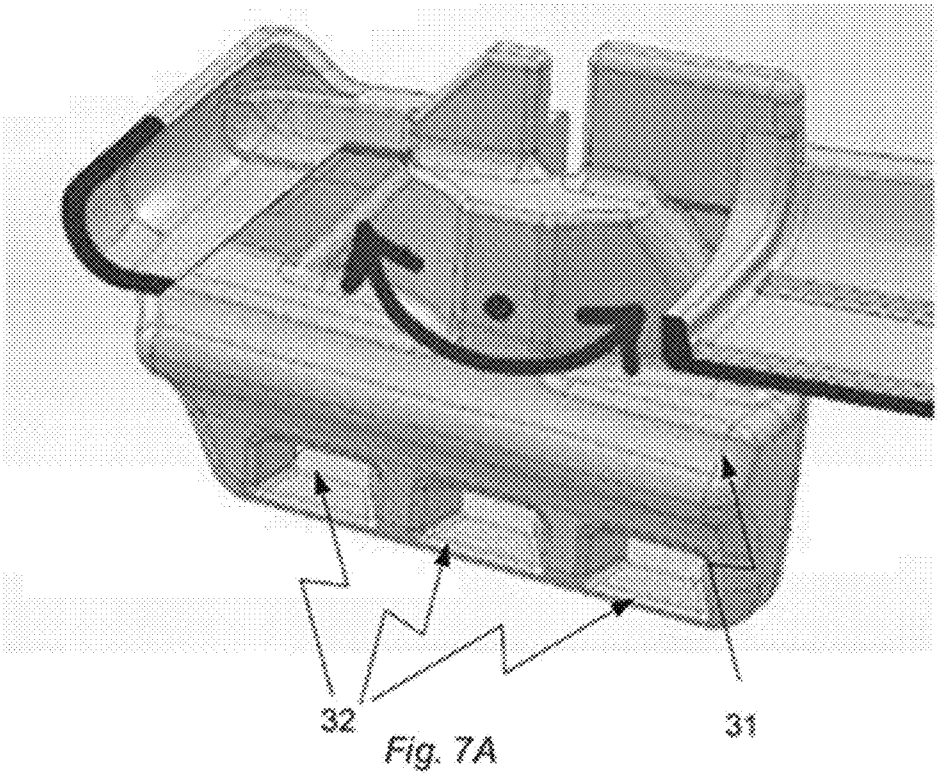
FIG. 7A illustrates a first flex pattern of the scanning-tip according to embodiments of the disclosure
Figure 7B:
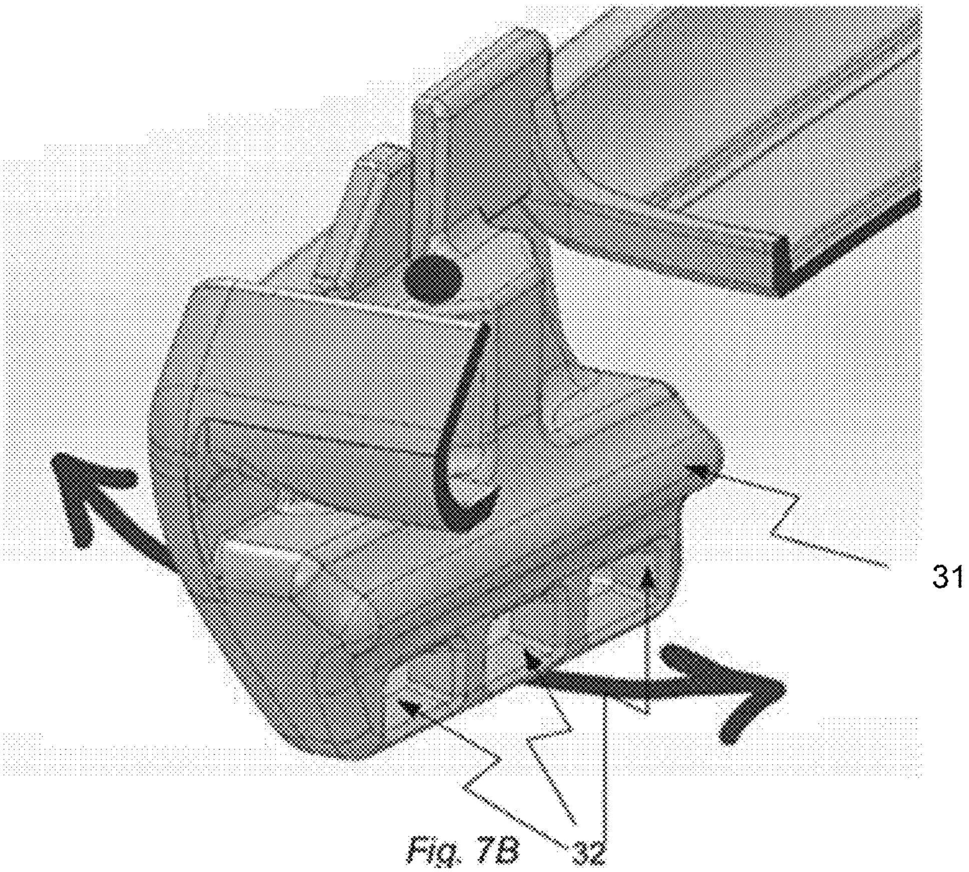
FIG. 7B illustrates a second flex pattern of the scanning-tip according to embodiments of the disclosure
Figure 8A:
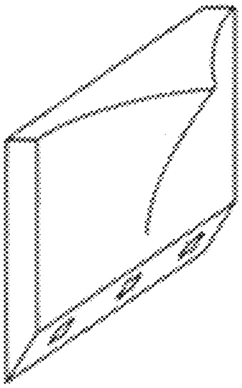
FIG. 8A-D shows pyramid-shaped light blockers according to embodiments of this disclosure
Figure 8B:
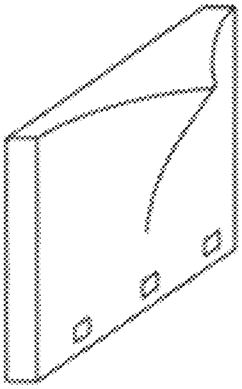
Figure 8C:
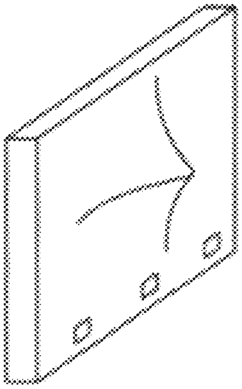
Figure 8D:
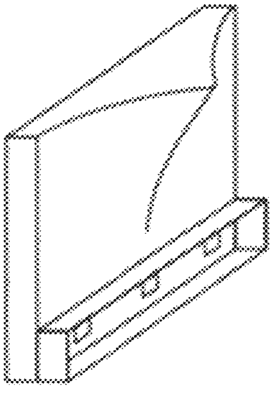

FIGS. 7A and 7B illustrate how the soft part 26 may be designed with two different flex patterns in mind. When the scanning-tip is installed on the scanner device, these two flex patterns are both in effect simultaneously.

The first flex pattern illustrated in FIG. 7A is rotational around the center part of the individual wings coming down at each side of the window opening. In essence, the upper center part of the wing holds more material compared to the sides to allow for this flex pattern to be dominant, but also to allow for the flex PCB to be fixated and run inside the silicone.

Having this flex pattern enables the center LED to be held in place, so that it is most likely to be situated on the gingiva. When the center LED is optimally placed, the outlying LEDs are less likely to dictate the position of the center LED and therefore they will all be positioned in the best possible way.

The second flex pattern illustrated in FIG. 7B is a bending of the whole wing from the soft part extremity point at the edge of the window opening. It can be thought of as a cantilever where the whole arm bends out as the light blocker protrusion is being positioned. The flex is predominant above the light blocker to allow for the best possible positioning of the LEDs on the gingiva within the teeth sizes in focus.

FIGS. 7A and B further shows light blockers 31 according to embodiments of this disclosure. In this embodiment, there is one light blocker 31 in the form of a long protrusion placed above the IR LED's on each side of the scanning-tip. This shape of the light blocker allows the user to randomly position the device within the part of the mouth in focus. To secure that the device is always resting on the bottom part of the teeth, or the top of the gingiva, when the device is positioned, it is designed so that the distance between the two light blockers on either side of the scanning-tip is less than the most narrow teeth in the part of the mouth in focus. In addition to the above-mentioned light blocker concepts, the IR LEDs may also be retracted into the soft part of the shell of the tip, as illustrated with the recesses 32. The protruded/overhanging part of the tip arm over the LEDs additionally functions to add to the light blocking. The three remaining sides around the LEDs may be slanted to allow for maximum light output into the gingiva.

FIGS. 8A-D shows another shape that may be utilized for the light blockers. In this embodiment, the light blockers are in the shape of a pyramid, which intuitively guides the user to position the device so that the interproximal area between the teeth is right under the center of the window opening. Various exact shapes of the pyramid structure can be envisioned, illustrated with figures A-D. In addition to the above-mentioned light blocker concepts, the IR LEDs may also be retracted into the soft part of the shell of the tip. The protruded/overhanging part of the tip arm over the LEDs additionally functions to add to the light blocking. The three remaining sides around the LEDs may be slanted to allow for maximum light output into the gingiva.

Figure 9:
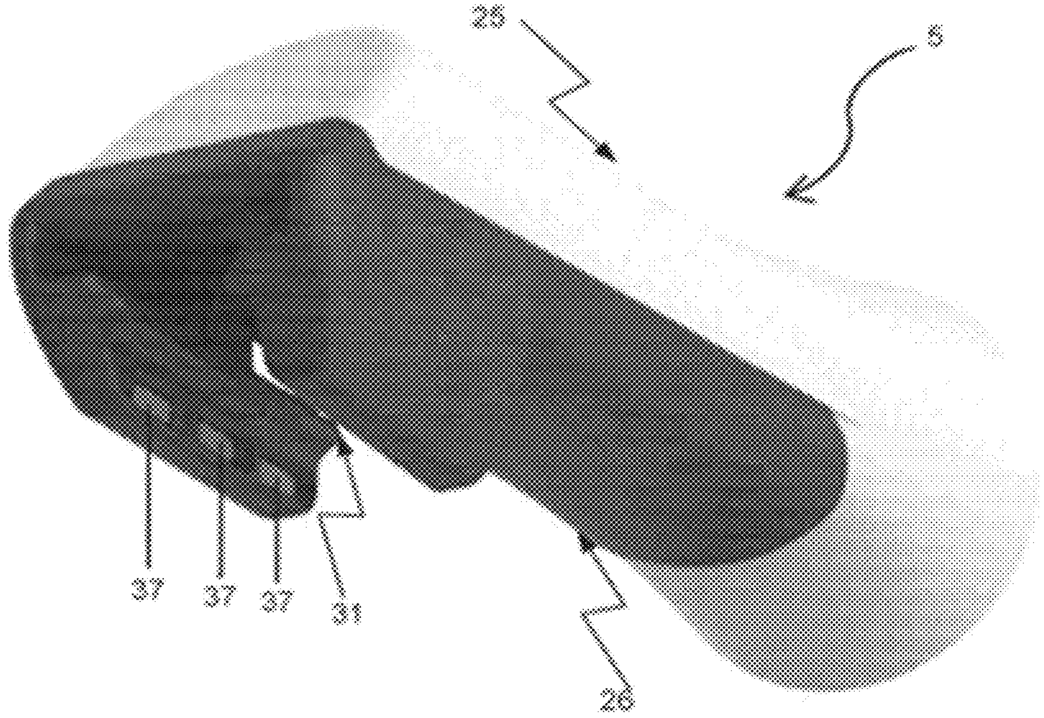
FIG. 9 shows an exemplary view of a scanning-tip according to embodiments of this disclosure

FIG. 9 shows a view of the scanning-tip 5 according to embodiments of this disclosure. The recessed IR LEDs 37 and the light blocker protrusion 31 is shown. The soft part 26 and the hard part 25 of the shell of the scanning-tip, are also shown.

Figure 10:
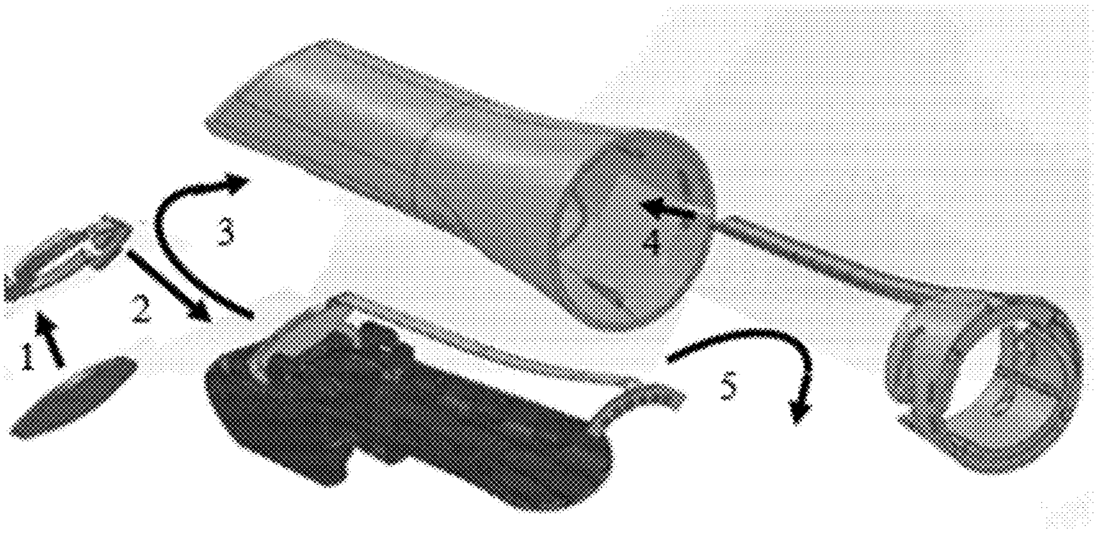
FIG. 10 illustrates an assembly method according to embodiments of the disclosure

FIG. 10 shows a stylized view of the assembly method of the scanning-tip according to embodiments of this disclosure.

Figure 11:
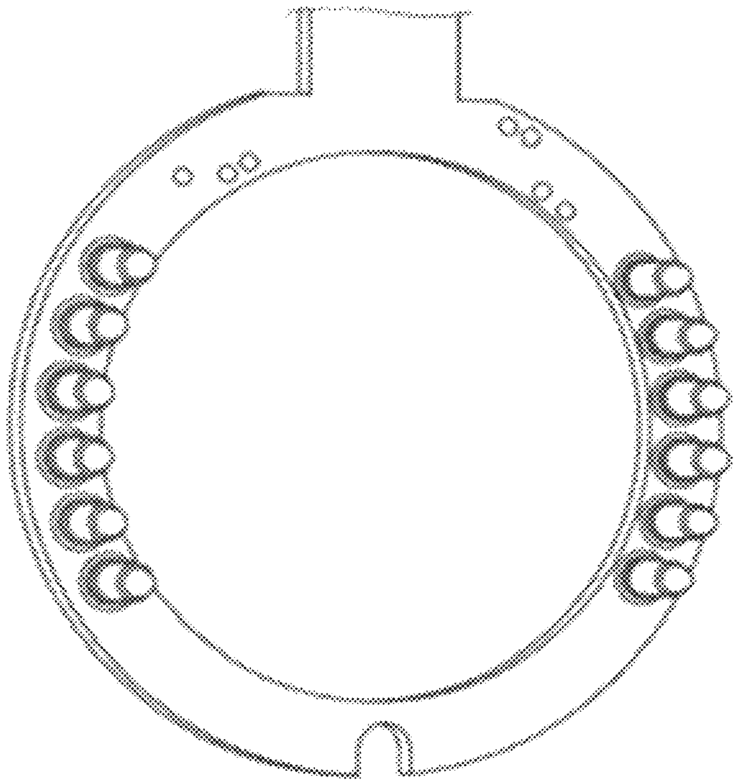
FIG. 11 shows connectors between the scanning-tip and the scanner device according to embodiments of the disclosure

FIG. 11 shows a plurality of connectors between the scanning-tip and the scanner device according to embodiments of the disclosure, here illustrated as pins. The plurality of connectors are located at the proximal end of the scanning-tip.

Figure 12A:
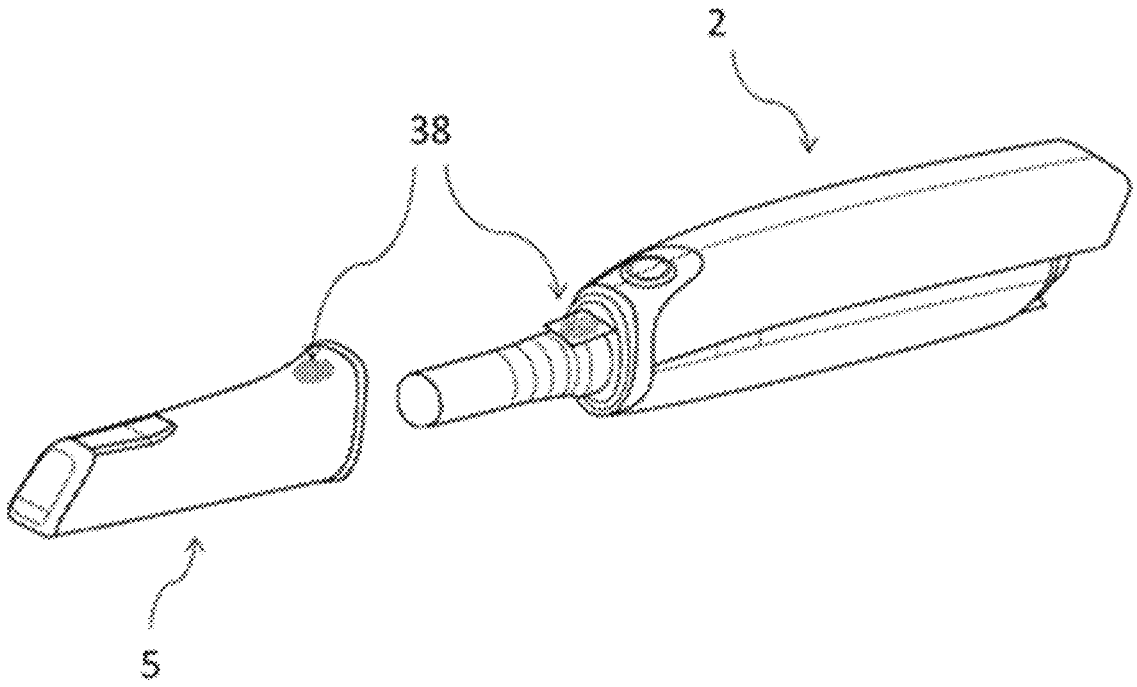
FIG. 12A shows a scanning device and replaceable scanning tip according to embodiments of the disclosure

In another aspect illustrated in FIG. 12A, the intraoral scanner system comprises an intraoral scanner 2 and a replaceable scanning tip 5 adapted to fit over the distal end of the scanner and to direct probe light from the scanner towards the object to be scanned. The tip is replaceable for hygienic purposes, as it is common practice to remove the tip between treatments and clean and sterilize it before the next treatment. Scanner systems typically ship to end-users with 2 or more tips so the user can use a clean tip on a patient while others are being cleaned. This enables an uninterrupted workflow throughout a typical workday.

A scanning tip 5 may be designed as an active unit requiring power and data exchange. Physical contacts require protrusion of conductors through the scanner body enclosure for transfer of electrical energy. The cavities introduced around the protrusions are prone to ingress of biological matter and bacteria, making it a challenge to ensure proper cleaning and disinfection of said cavities.

In these embodiments, the scanner system is designed such that it provides the possibility of exchanging electrical contacts with a magnetic inductive interface 38 which is able to provide both power and/or data exchange between the scanner and the active tip. It does so through magnetically coupled coils in an arrangement that is able to reduce the interference between the data transmission and the power transmission.

This solution has at least the following three major advantages;

1) eliminating the need for electrical contacts makes it possible to hermetically seal both the scanner and tip. This greatly reduces the challenges of cleaning and disinfection.

2) improved reliability—eliminating the need for electrical contacts will reduce the risks of mechanical wear. Electrical contacts are some of the points that are most likely to fail in a product. Due to mechanical wear, the contacts performance will eventually degrade to a point where the product seizes to function. In prior art systems, careful mechanical design takes this into account, by attempting to ensure that function seizure is postponed to a point after the expiration of the products service life. Despite this, design tolerances and improper testing methods during development in combination with unintended user actions or unforeseen operating environmental conditions impose risks of premature failure.

3) reduce the complexity and size as mechanical contacts require moving parts and demand higher mechanical complexity. Reducing the mechanical complexity allows for a more compact design.

The solution comprises a power coupling mechanism and/or a communication coupling mechanism.

The solution may be based on near field magnetic induction and can be realized in different manners.

Power transmission and communication may be either performed simultaneously or separately during time periods of exclusivity to one or the other mechanism.

Figure 12B:
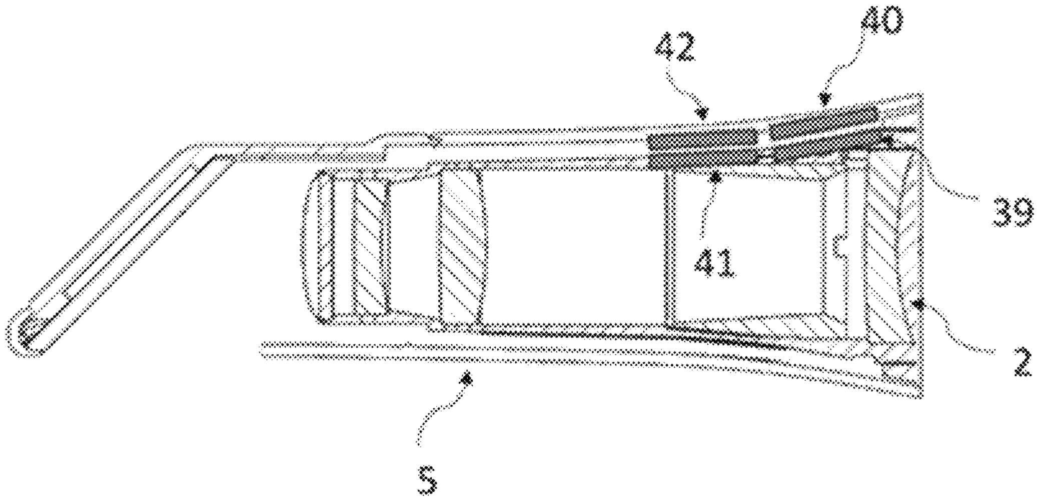
FIG. 12B shows a configuration of magnetic induction coils according to embodiments of the disclosure

One configuration is displayed in FIG. 12B, showing the front part of the scanner system with the tip 5 mounted on the distal end of the scanner 2.

The power transfer is based on the physical property of magnetic inductive coupling between adjacent coils of conductors. A supplied alternating electrical current in one coil (hereafter referred to as the TX coil 39) induces a current in the second coil (hereafter referred to as the RX coil 40) due to the magnetic coupling between said coils. The coupling k is dependent on the relative positioning of the coils as well as the geometry of said coils. A non-exhaustive list of various coil configurations are described below:

A set of circular, oval or rounded-edge rectangular planar or non-planar coils either parallel or placed at an angle relative to each other, with their geometric centers aligned or close thereto (shown in FIG. 12B).

A set of circular, oval or rounded-edge rectangular planar or non-planar coils formed to conform to a circular shape such as a tube, with their geometric centers aligned or close thereto.

A set of concentrically helical coils of different diameter placed with their geometric centers aligned or close thereto.

All configurations could be with or without a ferrite sheet backing to guide the magnetic field.

The coil pair is operated by application of an alternating voltage or current to the TX coil generating an alternating magnetic field inducing a current in the RX coil. The induced current can be further conditioned in the accessory to provide a stabilized DC voltage supply.

The system efficiency in terms of power transfer is partly dependent on the losses in the voltage conditioning circuit in the accessory. A difference between the voltage level received by the accessory and the voltage output of the conditioning circuit imposes losses proportional to the loading current of electronics contained in the accessory. Therefore, it is practical to be able to adjust the amplitude of induced current in the RX coil to match the immediate load condition. The accessory may be able to feedback information on the immediate voltage amplitude to the device and the device may adjust the power accordingly by adjustment of either amplitude or frequency of the AC signal applied to the TX coil.

The communication is additionally based on the physical property of magnetic inductive coupling between adjacent coils of conductors. A supplied alternating electrical current in one coil induces a current in the second coil due to the magnetic coupling between said coils.

The communication coil on the scanner device side will be referred to as the MST coil 41, and the coil on the tip side will be referred to as the SLV coil 42.

The operating mode of the coil pair is by application of a frequency, phase or amplitude modulated alternating voltage or current to either the MST coil 39 by the device or the SLV coil 40 by the tip. The applied signal generates an alternating magnetic field inducing an electrical signal current in the receiving coil which may be either the MST or SLV coil depending on the direction of communication (scanning device to scanning tip or scanning tip to scanning device). The induced signal is demodulated according to the employed modulation scheme by the recipient.

The communication mechanism may be either one of the methods described above or a combination of both.

The inductive communication mechanism may be based on either a dedicated communications coil or on basis of the same coil set that the power transmission mechanism employs. The solution may thus comprise either:

4 coils, where TX and RX are used for power and MST and SLV are used for communication or 2 coils, where TX is the same as MST and RX is the same as SLV and vice versa.

Figure 13A:
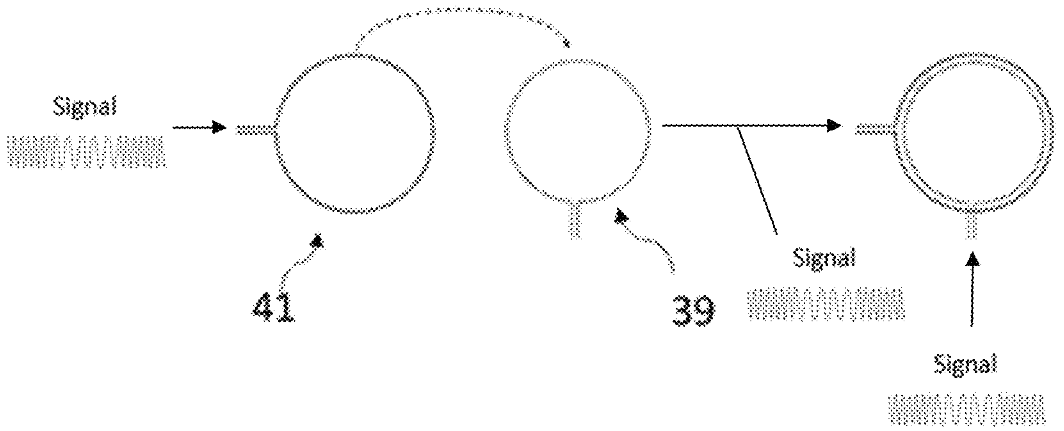
FIG. 13A-C shows various induction coil designs according to embodiments of the disclosure
Figure 13B:
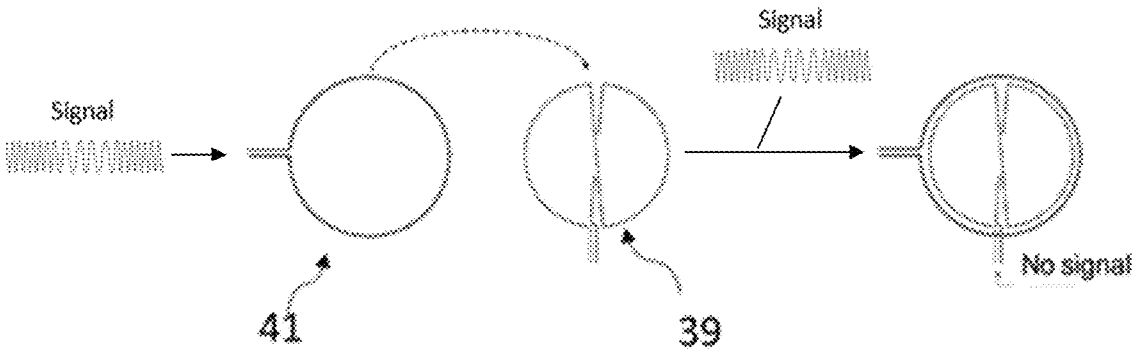
Figure 14A:
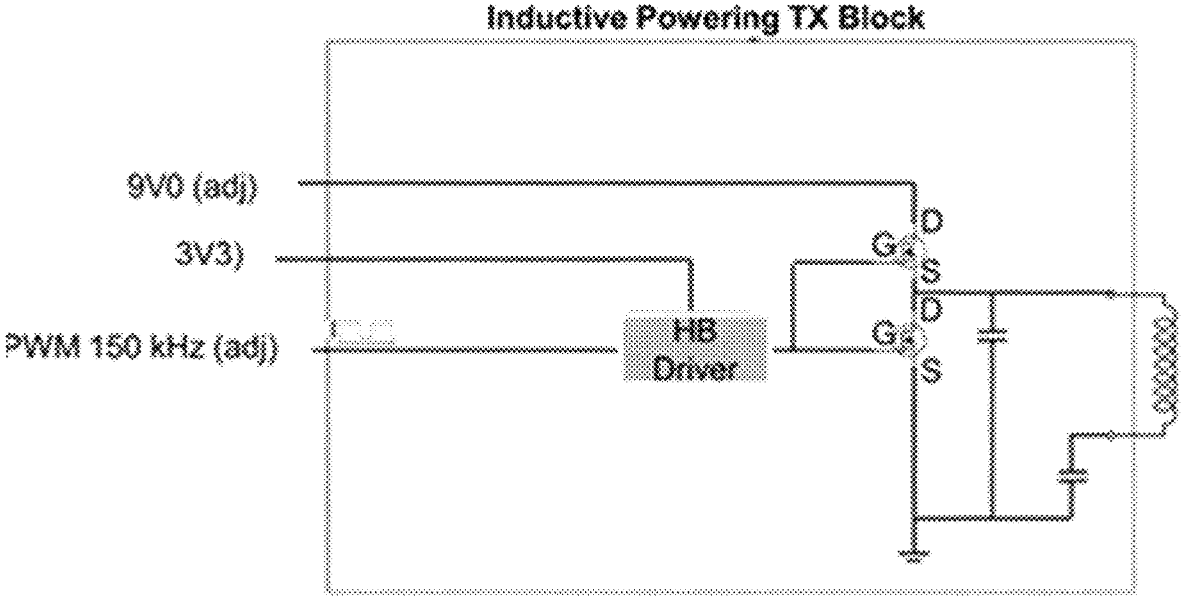
FIG. 14A-B shows block diagrams of coil circuitry according to embodiments of the disclosure
Figure 14B:
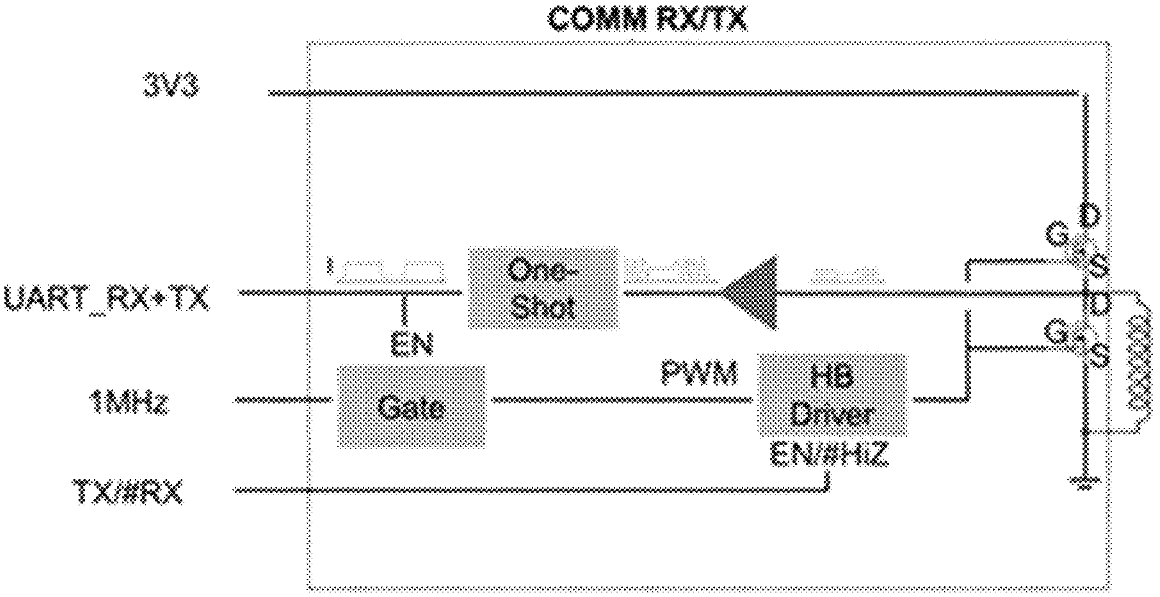

The design of 4 coils is shown in FIG. 13*a* for the interface on the scanner side. In this case the magnetic field from the TX and RX coils may contribute to a significant noise signal on the MST and SLV coils. A method to eliminate interference from the adjacent alternating magnetic power transmission field, a special communications coil geometry may be utilized as shown in FIG. 14*b* (only displaying one side of the induction interface). The geometry is such that both communications coils 41 and 42 (not shown) are twisted 180 degrees around a symmetrical center creating two halves resulting in a shape of 8. In such a configuration, placing the communications coil 39 in a uniform, alternating field such as the power transmission field 41 would cause the induced signal in the communications coil to cancel out due to the opposite polarity of the induced current localized to each half of two twisted coils.

By employing the same twisted geometry on both the MST and SLV coil, an applied communications signal would not cancel out due to the identical localized polarity of each half of both coils. This communication arrangement is displayed in FIG. 13*c*.

In the case of only 2 coils, the communication channel may be realized by a frequency, phase or amplitude modulated signal which is placed in another frequency band than the power transfer AC signal.

The communication may also be implemented by modulation of the frequency of the supplied power transfer AC signal (by the device) and load modulation from the receiving side.

The coils can be placed in different locations of the scanning system. In the image in FIG. 12B, possible placements are shown for a set of circular planar coils placed parallel to each other. The illustration is based on the 4-coil solution.

Another implementation comprises concentrically helical coils, where the coils are two solenoids. One solenoid being part of the tip, while the other solenoid is running inside the first one and being part of the front tube assembly.

For any chosen solution, the power transmitting coil may be connected to one or more capacitors in either series or parallel or a combination hereof, constituting what shall hereafter be referred to as a coil assembly. The capacitance along with the inductance of the coil determines the resonant frequency of the coil assembly.

The power transfer coil may be driven by either a half or full bridge at a frequency above or below the resonant frequency of the coil assembly. The power transfer between the coil assemblies increase as the frequency of the applied AC signal approaches the resonant frequency of the coil pair. Therefore, it is possible to adjust the power transfer to match the requirement of the receiving devices by modifying the frequency of operation.

Another means of adjusting the power transfer is by changing the amplitude of the AC signal supplied to the TX coil.

On the receiving side of the power transfer, the induced current may be rectified either passively through a diode bridge or actively though transistor full bridge. The voltage conditioning may be done either via a switched mode power converter or an LDO.

An LDO solution is preferred for its smaller solution size and we will handle the E×I losses by means of power transfer governance using the communications mechanism. To reduce the voltage overhead, the key difference between Qi and the 3S derivative is thus the addition of a dedicated communications physical layer for the power arbitration. A block diagram of the transmitter coil excitations circuit can be seen in FIG. 14*a*.

The communication may be based on UART. Standard UART implementations consist of dedicated RX and TX lines, but can be implemented in loop-back mode requiring only a single shared physical medium. Limiting the protocol to loopback requires that whoever is transmitting ignores the immediately looped back echo, and the implementation will have a dedicated master to initiate all communications to avoid collisions.

Pulse duration (t_os) is set at 1.25 times the period of the carrier wave so the oneshot is continuously retriggered by the carrier wave before its pulse duration expires. When triggered, the one-shot output indicates a logical 1.

Only when the carrier wave has not retriggered the one-shot within the pulse duration period will the one-shot output stabilize to indicate a logical 0. The logical output states may also be inverse to the presence of carrier wave.

FIG. 14*b*, shows an implementation on the device side, where the processor on the mainboard of the scanner generates the logical signaling. On the receiving side, a standalone uController provides this functionality. Other than that, the solutions share the same features.

The communication may be based on an On-Off keyed carrier wave. Demodulation requires an envelope tracking circuitry to decode logical levels from the On-Off keyed carrier wave. A one-shot retriggerable monostable multivibrator such as SN74LVC1G123 may be used for the purpose. The pulse duration means that there will be a delay (t_delay) from when the carrier wave disappears until the data line goes low. Using a 1 MHz carrier wave with a corresponding period of 1 μs, a worst-case delay on the output of the one-shot is 1.25 μs. UART accuracy requirement of 1.5%, imposes a minimum carrier wave burst length duration of 1.25e-6/0.015=83 μs, corresponding to a baud rate of 12 kHz.

In this implementation, the use of a uController on the receiving side may be used.

Another option is to use an NFC tag (RFID) and reader solution to act as a transparent I2C bridge for communication between scanner and tip. In this case the communication would be for example 13.56 MHz amplitude shift keying as is the standard for NFC. The device would host the reader and the accessory would host the tag. For this solution the NXP NTAGS family of tags are under consideration. The area consumption on the accessory side would be modest, but significant on the device side. This would imply a data transmission rate p in the 10-100 kbit/s range.

This option is based on the 1-wire protocol where the device acts as host and a MSP430 is placed in the receiving side. An MSP430 may act as a 1-wire slave as described in this (TIDUAL9A—June 2016—Revised July 2016 Submit Documentation Feedback Copyright © 2016, Texas Instruments Incorporated Memory Emulation Using 1-Wire® Communication Protocol) application note. The MSP430 would handle further communication with any additional hardware in the tip through downstream I2C slaves and also provide GPIO's for multiplexing potential LEDs so the need for a dedicated chip for that purpose would be eliminated. This solution is a little laborious in development but physically small once implemented. Alternatively, the receiving side could host a 1-Wire-to-I2C Master Bridge such as the Maxim DS28E17. This solution is less adaptive on the accessory side and may impose difficulties in maintaining the 1-Wire timing. DS2482X-100+T is alt.

Figure 13C:
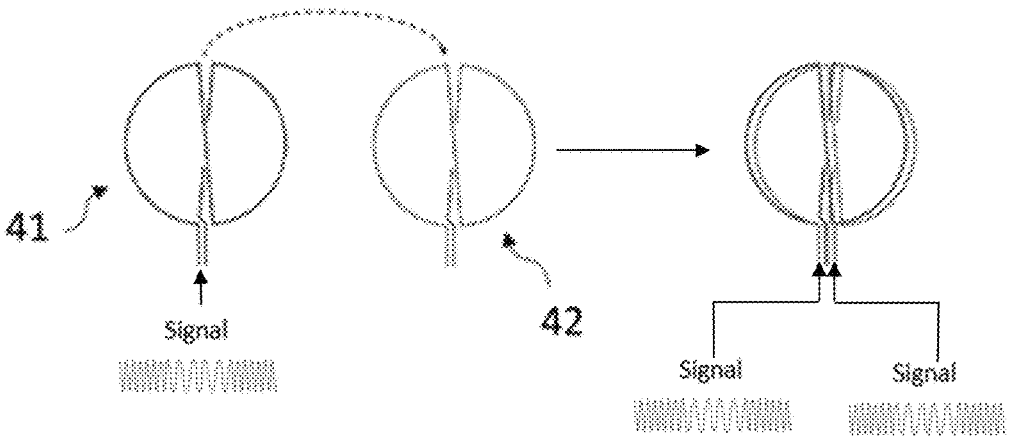

Alternatively, the communication may also be implemented by modulating IR, UV or visible light from either the device to the tip, tip to device or both. The physical implementation is by LEDs on the transmitting side and optical sensors on the receiving side. The device and accessory may then encompass for communication either a LED, optical sensor or both depending on the mode of communication implemented. It is also possible to use a Bluetooth System-on-Chip such as the DA14531 from Dialog Semiconductor. The antenna could then be implemented as shown in FIG. 13*c*. An advantage of this solution is the high data rate which would enable the use of external cameras in the tip and other high data rate features.

Figure 15:
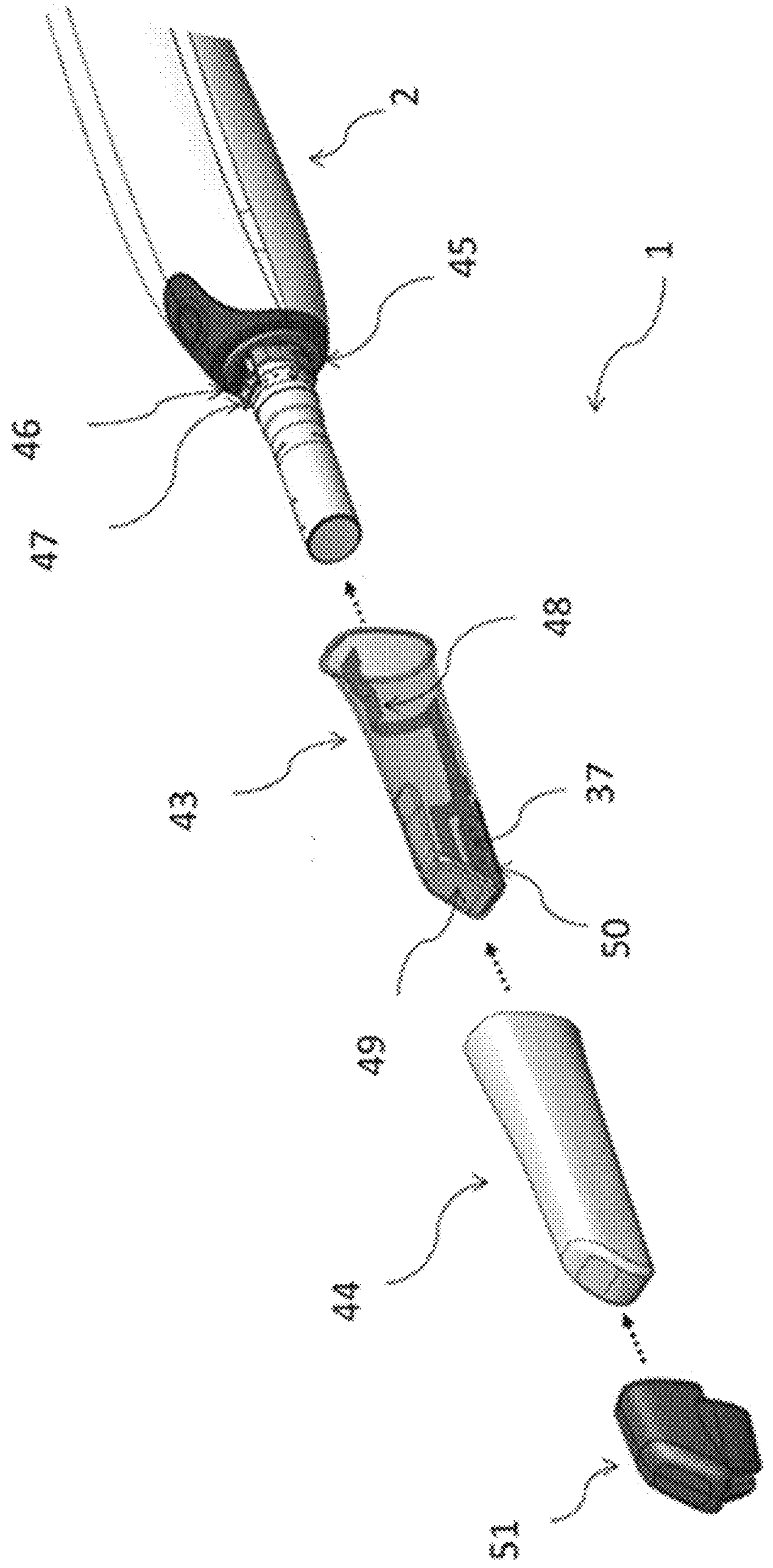
FIG. 15 shows a scanning system according to embodiments of the disclosure

In another example displayed in FIG. 15, show a scanning system 1 with a scanning device 2 configured with a manufacturer-detachable-scanning tip 43 mounted to the scanner body in such a way that during normal operation of the scanner, the manufacturer-detachable scanning tip is practically stationary situated over the distal part of the scanner, hence extending the scanner body into a front assembly containing essential optical elements. The term manufacturer-detachable is used synonymously in this disclosure with the term semi-replaceable. This results in a semi-integrated scanning head providing specific functionality to the scanning device. The scan head may be detached from the main body 2 and replaced with another scan head by a technical skilled person following a specific operational procedure. During everyday operation the scanner-head 43 is however considered to be permanently secured and sealed during operation of the scanner. The scan head is configured to couple with a hygiene sheath 44 fitting tightly at least around the scan head creating a microbial barrier, such that only the hygiene sheath 44 needs to be sterilized or replaced in-between different patients. Such a configuration enables the scan-head to only require medium level cleaning with proper wipes.

A reusable mechanical seal 45 between the scan head and the scanner body 2 ensures that the microbial barrier can be re-established successfully after the scan head has been replaced there by eliminating the need for any disinfection of the scanner front tube.

The tip interface of the scanning device is configured with a service connector interface 46 and proximity sensors (for example hall sensors) 47 to enable detection of which sleeve type is used over the scanner when the scan head is mounted. The service connector interface is configured to couple with the connectors on the Printed Circuit Board (PCB) 48 located inside the scan head.

The scan head comprises an optical element 49 to direct probe light from the scanner body towards the object to be scanned along with an optically transparent window 50 or a prism element for sealing the inside of the scan head from coming in contact with the outside environment while not effecting the probe light of the scanner. This secures against any contamination of the interior of the scan head and the front part of the main scanner body.

In one configuration shown in FIG. 15, the scan head 43 is configured with a mirror 49, a transparent window (for example sapphire glass and a quarter wave plate) 50 configured to transmit the probe light from- and to the scanner and a flexible PCB 48 with a dedicated heating element for heating (ITO, resistive heater, or an inductive heater) the window in the scan head. Additionally, IR light sources 37 may be attached to the PCB. The PCB may also contain a multiplexer for individual IR led control. These IR LEDs 37 may be located in two arrays of 3 IR LEDs located on each side of the scan head 43.

The scan head 43 is configured to couple with a multiuse hygiene sheath 44 for standard scanning, however the upon identification of an additional IR adapter 51, which is configured to fit outside of the hygiene sheath over the scan head, the scanner identifies the presence of the IR adapter and instructs the processor to enable a dedicated IR scan mode. Such identification could be by recognizing part of the IR adapter with in the FOW of the scanner, thereby instructing the processor to initiate the dedicated scanning mode.

In some embodiments, the IR adapter 51 shown in FIG. 15 is constructed to passively direct IR light from the scanner head 43 and into the teeth and/or the gingiva to provide an IR transillumination examination of a patient's teeth. The IR adapter is configured to guide the light from the LEDs trough the structure. This implies that there will be a coupling of light from the scan-head 43 to the passive IR adapter 51 part. This coupling could happen through the hygiene sleeve 44. Some design considerations for such a solution include but are not limited to:

The loss of light should be as small as possible, because losses mean that the LED(s) would have to emit more optical power thus using more electric power. In some embodiments, the scanning device may be wireless, hence powered by one or more batteries. In this case, it is especially important to conserve the power usage to extend the usable scanning time before having to recharge or change batteries.

The total electric power which can be used by the scanner is limited. LEDs emit heat too and the outer surfaces of the tip should not reach temperatures above 41° C., due to safety regulations and patient comfort.

The light exits the IR adapter device such that the whole field of view of the scanner is illuminated well. The IR adapter should be made such that it can withstand frequent sterilization cycles, such as autoclave or high-level disinfection in between use.

The IR adapter outer surface should preferably be smooth and not feature cavities on the outside. The IR adapter should be made from biocompatible materials.

The shell of the IR adapter 51 may consist of one machined or molded part. Alternatively, the IR adapter may be assembled or manufactured from two or more injection mold shots or machined parts with different softness. The durometer shore hardness value of the softer material used could be A40-A80. This makes the material smooth and pleasant for the patient when the IR adapter is placed in the patient's mouth during scanning. The IR adapter 51 could also comprise one or more additional rigid parts such as a frame stabilizing the construction, directing the light and configured to snap to the shell for attachment.

As for the choice of LEDs 37, the following criteria should be considered: Efficiency of electrical to optical power transformation, geometrical emission profile and how well it allows coupling to a light guide, size and heat formation.

The IR adapter 51 may comprise two flexible wings allowing the device to fit various oral cavities and teeth sizes.

The part of the IR adapter 51 coupling to the scanner-head may have incorporated grooves and interaction surfaces at the side of the shell to mechanically guide and ensure correct attachment between the IR adapter 51 and the rest of the tip assembly, i.e. scan-head 43 and hygiene sheath 44.

In some embodiments, the IR adapter 51 is made to guide the light from the LEDs through the structure.

Figure 16A:
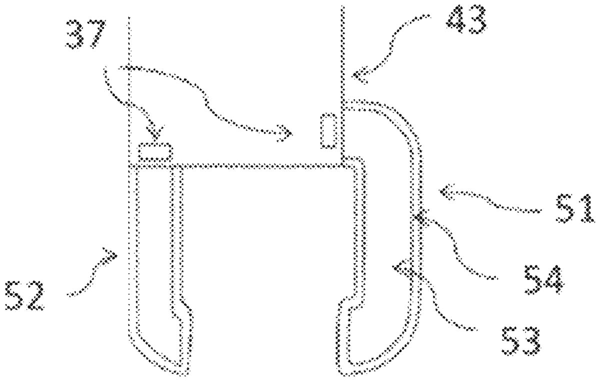
FIG. 16A-C illustrates light guide designs according to embodiments of the disclosure

As illustrated in FIG. 16*a*, in some embodiments the light guides, or light pipes, or optical fibers, or waveguides 52, may be based on the principal of total internal reflection and feature a core 53 and a cladding material 54, where the refractive index of the core is higher than the refractive index of the cladding. Both materials should at least be optically transparent for the respective wavelength emitted by LEDs 37, typically IR light at 850 nm, but wavelengths from 750 nm to 950 nm could be possible, and even longer wave-lengths can be used if desired.

Figure 16B:
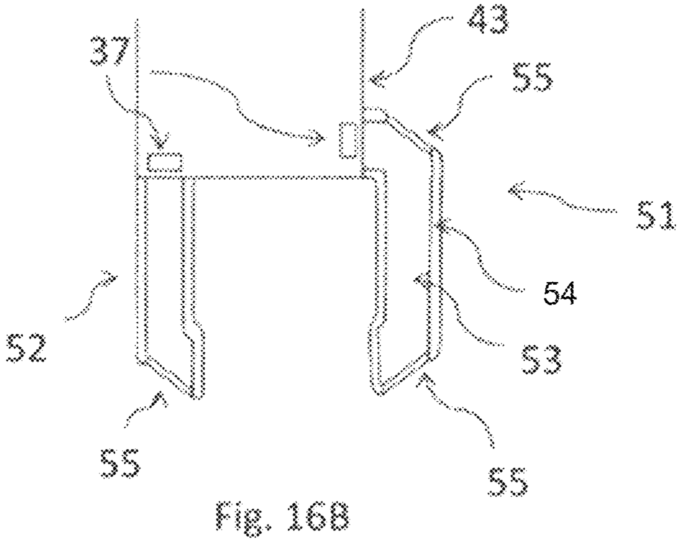

In other embodiments as shown in FIG. 16*b*, the light guides may be based on mirrors 55 reflecting light from a reflective surface, such as metal mirrors (e.g. gold), mirrors based on total internal reflection, or dielectric mirrors made from thin layers of dielectric materials. The main performance criterium in this context is high reflection.

Due to losses at the bends/mirrors a solution with only one bend may be beneficial. Light guide losses can be high for bended light guides, especially if the index contrast between cladding and core is small and the bending radius is high. Thus, mirrors are often used for reflection light instead. Such mirrors can be based in the principles above, where mirrors based on total internal reflection are not very efficient if the angle is high and the index contrast low.

Figure 16C:
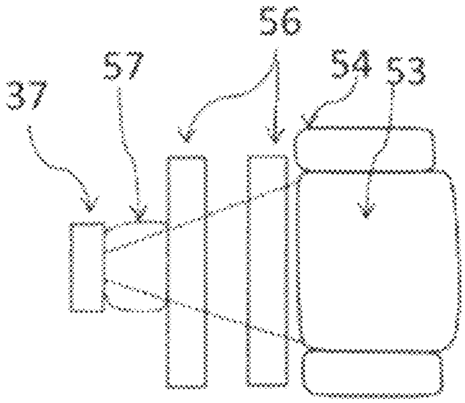
Figure 17A:
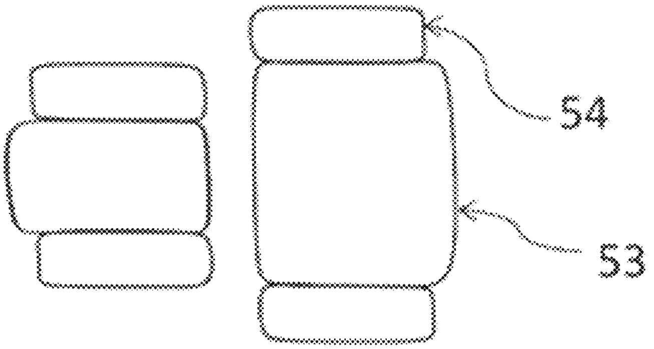
FIG. 17A-D illustrates light coupling designs according to embodiments of the disclosure
Figure 17B:
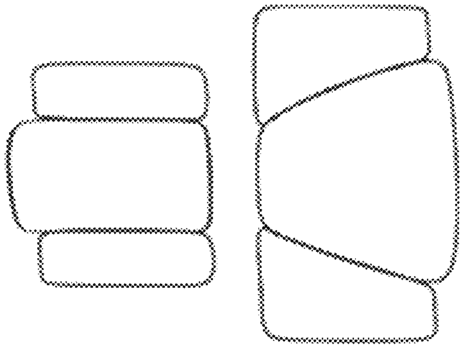
Figure 17C:
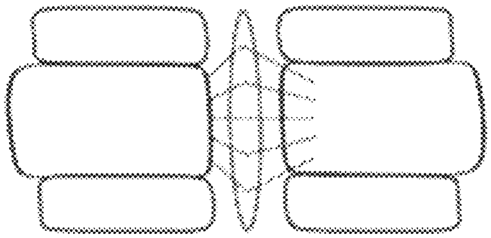
Figure 17D:
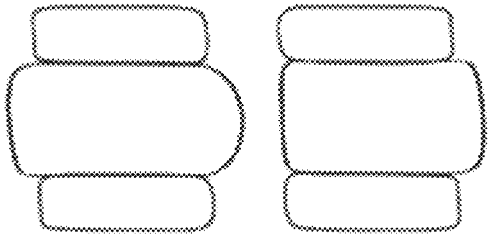

In the scanner configuration shown in FIG. 15 light must be coupled from the LED to the light guide. If the flexible part is not separated from the scan tip, only one coupling is necessary. However, if the parts are separated, for example by a hygiene barrier a second coupling is necessary. In this context, it is possible to separate the parts between the LED and the light guide. In such a case, windows 56 may be introduced between the light guide and LED(s) as illustrated in FIG. 16*c*. In this case, coupling will in general be more efficient if the distances and thicknesses are small and if refractive index differences are small in order to minimize loss due to reflections from the window surface. The latter can be achieved by filling air gaps with transparent material 57.

The windows 56 can also be formed as lenses in order to make the coupling more efficient. Such windows/lenses can be made from polymers or from glass. The separation between the tip part and the part touching the patient can also be made such that the light is coupled from the LED 37 to a first light guide, and from the first light guide to a second light guide in the outer part after-wards. In such a second coupling, the gap between the two guides is critical: The smaller the gap is, the higher the coupling efficiency. The alignment of the two light guides in the vertical direction is also very critical for the coupling losses. In addition, the coupling efficiency can be improved by having the second light guides with a different shape than the first light guides.

FIG. 17A-D illustrate different improved light coupling designs. Better coupling efficiency can be achieved if the second core is larger, FIG. 17A. In addition, the shape of the second light guide can be tapered as sketched in FIG. 17*b*. Such a shape can be beneficial, as the light shall be spread within the light guide to achieve illumination of a larger volume in one of the directions (i.e. where multiple LEDs are used).

The coupling efficiency between two light guides can be improved be introducing a focusing element, such as a lens. Such a lens could be formed separately next to a window, or as the window between the two light guides, FIG. 17*c*, or as the out shape of the light guide, FIG. 17*d*. The coupling from the LED 37 to a light guide 52 is generally more efficient the closer the LED is placed to the light guide. Alignment in the lateral directions is critical and can be improved by a larger light guide core compared to the size of the LED. In addition, a tapered light guide can be used to improve coupling efficiency and to change the shape and size of the light guide.

The wave guides can either be built as individual constructions projecting light from individual LEDs, but they can also be built collectively transporting light from one or more LEDs carrying light to individual exit points.

Figure 18A:
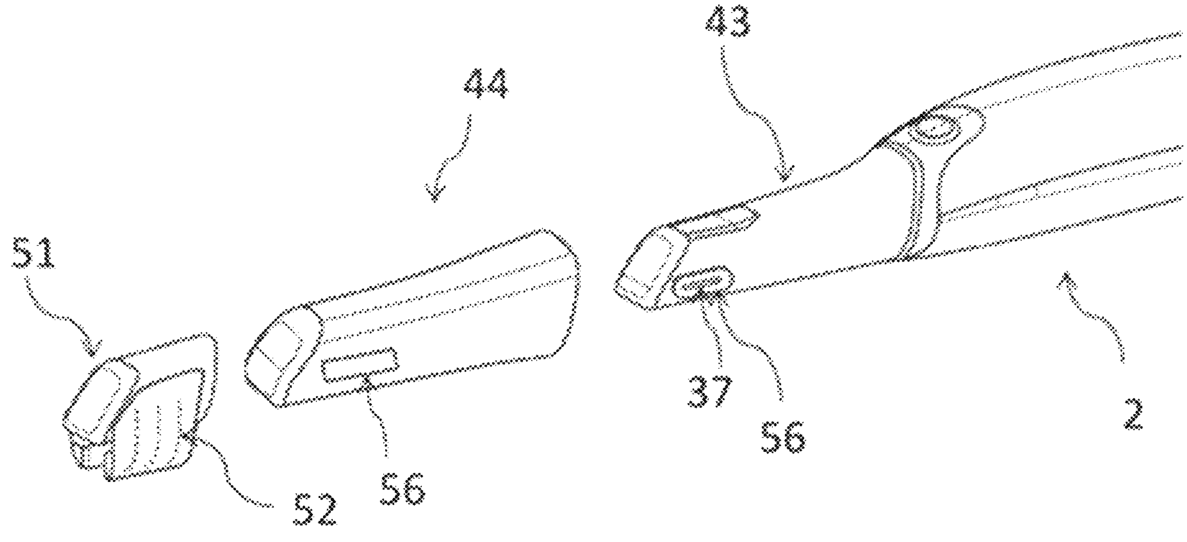
FIG. 18A shows a scanning system according to embodiments of the disclosure

Illustrated in FIG. 18A is another embodiment of the scanning system, where the scan-head 43 comprises IR light sources 37 in the distal end and is connected to the scanner 2. The IR light sources are protected by a window 56. The system is configured to couple with a multi-use hygiene barrier sheath 44. The hygiene sheath 44 additionally comprises a coupling window region 56 allowing IR light to be transmitted through the sheath. Additionally, an IR adapter 51 is configured to fit over the hygiene sheath when mounted on the scanner, in order to couple IR light from the scan-head into light guides 52 transporting the illumination to the wing region where the IR light exits the structure.

Figure 18B:
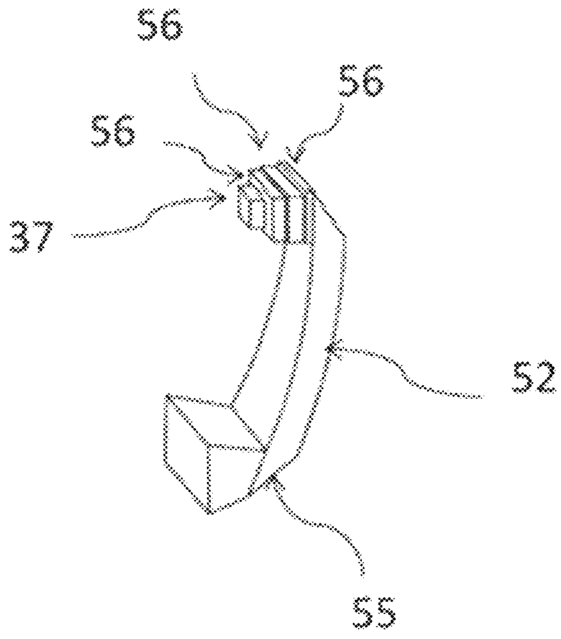
FIG. 18B illustrates details of a light coupling design according to embodiments of the disclosure

The details of a possible coupling arrangement can be seen in FIG. 18B.

A solution where the light sources are placed in the rear of the scanner-head 43 can be beneficial, because it allows to keep the mechanical dimensions of the distal end smaller, which is an advantage when scanning inside the oral cavity. In addition, the rear of the scan-head 43 may allow to use more space for the light sources and e.g. larger and/or higher power LEDs or lasers.

Light from the light source may be coupled to a tapered light guide. In these embodiments, a sheath window 57 is placed as part of the hygiene barrier sheath 44 or as a separate unit, which then allows the placing of a single-use transparent sheath on top. The light guide 52 is bended to guide the light down to the bottom end of the tip where it exits the tip. Losses can be high at the window due to coupling losses and reflections. Coupling losses can be minimized by precise control of the two light guides' positions with respect to each other. The window can be formed as a lens and the ends of the light guides can be formed as lenses. It can be beneficial to have two lens elements: One to collimate the light and one to focus the light.

Figure 19:
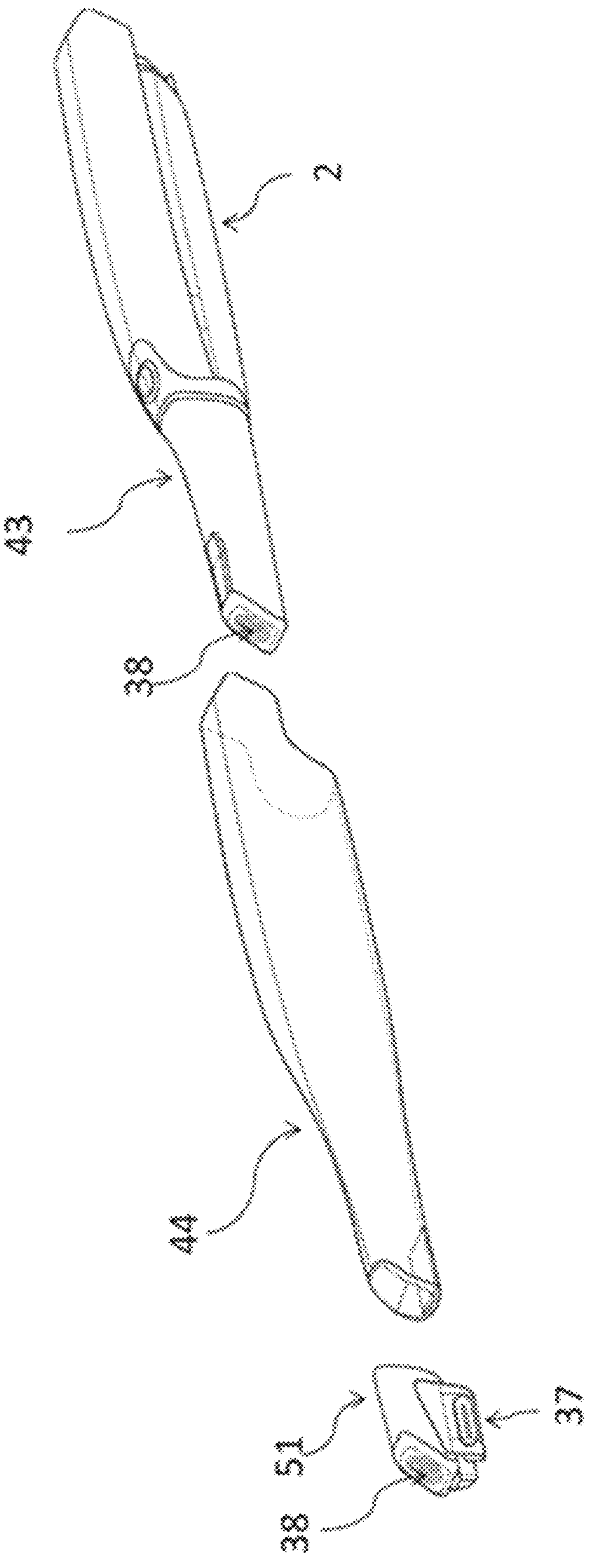
FIG. 19 illustrates a scanning system according to embodiments of the disclosure

In another configuration shown in FIG. 19, the scan head 43 is configured with a mirror 49, a transparent window (sapphire glass and quarter wave plate) 50 configured to transmit the probe light from- and to the scanner and a PCB 48 with a dedicated heating element for heating (ITO, resistive heater, or an inductive heater) the window in the scan head. Additionally, an inductive interface 38 is placed behind the optical element 49 on the scan head and also inside the IR adapter 51. The IR adapter 51 may contain one or more infrared light sources, such as two arrays of three IR LEDs 37 located on each side. The scan head 43 may also contain a multiplexer for individual IR led control. These IR LEDs 37 may be located in two arrays of three IR LEDs 37 in each of the wings. The induction interface 38 is configured to transmit both power for powering the IR LEDs 37 and data transmission for controlling the illumination. The IR adapter 51 is configured to fit over the distal end of the scan-head upon the placement of a hygiene sheath 44. In FIG. 19 the hygiene sheath illustrated is a single use sleeve, but multi-use sleeves or sheaths may also be employed.

The manufacturer-detachable scan tip 43 may provide several advantages over the easy on-the-fly detachable scan tip 5. It is designed for a simple hygiene barrier sheath. This reduces the complexity of the part of the scanner (i.e. Barrier sheath) which needs disinfection between patient. All optical elements as well as PCB heating elements and electrical connectors have been integrated behind a microbial barrier which ensures that these will not have to be designed for either manual cleaning/high level disinfection solutions or sterilizing in autoclave.

The fact that the optical element for directing the probe light toward the objects is protected inside the scan head 43 leads to longer lifetime and less decay of the optical element, thereby less need to perform frequent re-calibration adjustments when in operation or color corrections depending on the attached mirror in the tip 5. A scanning system adapted to the scan head 43 solution system may easily be upgraded to accommodate new functionalities and needs simply by replacing the scan head only. In case a scanner is accidentally dropped during operation, the front part of the scanner is often prone to be damaged causing the scanner device not to function properly. This type of damage often requires comprehensive repair at a dedicated technical facility. The disclosed scan head solution offers a way to absorb such impact energy and being easily replaceable afterwards. This makes repair of the scanner much faster with less inconvenience for the user as it can be carried out at the location of the user by a technical skilled person.

As the optical element for directing probe light towards the object to be scanned is confined with in the scan head 43 and not in a tip sleeve 5 no frequent color calibrations are needed as compared to an open tip containing an optical element.

In device claims enumerating several means, several of these means can be embodied by one and the same item of hardware. The mere fact that certain measures are recited in mutually different dependent claims or described in different embodiments does not indicate that a combination of these measures cannot be used to advantage.

Although the disclosure above has been described with respect to a replaceable scanning-tip for an intraoral scanner device, the principles therein may equally be employed in a scanner device with an integrated tip. For example, the principles of the dielectric coating, the materials of the tip, the construction and placement of the lightblocker protrusions, the placement of the IR LED's etc. may equally be provided in a scanner device with an integrated tip.

Although some embodiments have been described and shown in detail, the invention is not restricted to them, but may also be embodied in other ways within the scope of the subject matter defined in the following claims. In particular, it is to be understood that other embodiments may be utilized, and structural and functional modifications may be made without departing from the scope of the present invention.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and, in the following, may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. An intra-oral scanning system comprising:

a scanning device comprising a first magnetic induction coil, wherein the first magnetic induction coil is arranged at a distal end of the scanner device;

a scanning tip comprising a second magnetic induction coil, wherein the second magnetic induction coil is arranged at a distal end of the scanning tip, wherein the scanning tip further comprises an optical element located at the distal end of the scanning tip with a surface inside the scanning tip such that when the optical element receives light from a white light source located in the scanning device, the scanning tip provides white light to teeth, wherein the optical element is configured for receiving the white light as back-reflected from the teeth, such that when the optical element receives the white light from the teeth, the scanning tip provides the white light to a first image sensor in the scanning device;

the scanning tip being removeably connected to the scanning device;

wherein each of the first and second magnetic induction coils is configured to provide power transfer and/or a communication signal between the scanning device and the scanning tip during operation of the intra-oral scanning system.

2. The intra-oral scanning system according to claim 1, wherein the power transfer from the scanning device to the scanning tip comprises supplying an alternating voltage or electrical current in the first magnetic induction coil, thereby inducing an electrical current in the second magnetic induction coil.

3. The intra-oral scanning system according to claim 1, wherein providing the communication signal between the scanning device and the scanning tip comprises providing a frequency, phase or amplitude modulated alternating voltage or current to either the first magnetic induction or the second magnetic induction coil, thereby inducing a modulated signal in the other of the first magnetic induction or the second magnetic induction coil, wherein the modulated signal comprises the communication transfer from the scanning device to the scanning tip or from the scanner tip to the scanning device.

4. The intra-oral scanning system according to claim 3, wherein the intra-oral scanning system is configured to demodulate the modulated signal.

5. The intra-oral scanning system according to claim 1, wherein the communication signal is placed in a frequency band that differs from a frequency band of a power transfer signal related to the power transfer.

6. The intra-oral scanning system according to claim 1, wherein:

the scanning device further comprises a third magnetic induction coil;

the scanning tip further comprises a fourth magnetic induction coil;

wherein the first magnetic induction coil and the second magnetic induction coil are configured to provide the power transfer, and the third magnetic induction coil and the fourth magnetic induction coil are configured to provide the communication transfer.

7. The intra-oral scanning system according to claim 6, wherein the third magnetic induction coil or the fourth magnetic induction coil is twisted 180 degrees around a symmetrical centre, the third magnetic induction coil and the fourth magnetic induction coil thereby comprising two halves in the shape of a figure-eight.

8. The intra-oral scanning system of claim 1, wherein the surface is a window or a mirror.

9. The intra-oral scanning system of claim 8, wherein the mirror comprises a dielectric coating.

10. The intra-oral scanning system of claim 1, wherein:

the scanning tip is a replaceable scanning tip or a semi-replaceable scanning tip.

11. The intra-oral scanning system of claim 10, wherein the intra-oral scanning system includes an infrared adapter configured to attach to the scanning tip, the infrared adapter comprising at least a second magnetic induction coil and at least one infrared light source, wherein when attached to the scanning tip, the second magnetic induction coil is arranged at a distal end of the scanner device, wherein the infrared adapter is configured to attach to the scanning tip by snapping and/or sliding onto the scanning tip.

12. The intra-oral scanning system of claim 11, further comprising:

an infrared light source configured to emit infrared light.

13. The intra-oral scanning system of claim 12, further comprising an optical element configured for receiving the infrared light as back-reflected from the teeth, such that when the optical element receives infrared light from the teeth, the scanning tip provides infrared light to an image sensor.

14. The intra-oral scanning system of claim 12, wherein the scanning tip further comprises one or more light blockers at the distal end of the scanning tip, said one or more light blockers being configured to block direct and or indirect stray light.

15. The intra-oral scanning system of claim 14, wherein the infrared light source comprises a plurality of infrared light sources located at said light blockers.

16. The intra-oral scanning system of claim 14, wherein said light blockers are formed as a protrusion placed above the infrared light source.

17. The intra-oral scanning system of claim 12, wherein the scanning tip further comprises a printed circuit board configured to provide electricity from the scanning device to the infrared light source.

18. The intra-oral scanning system of claim 11, further comprising one or more light guides for guiding the infrared light from the scanning tip to the teeth and/or gingiva.

19. The intra-oral scanning system of claim 18, wherein the one or more light guides comprise a core and a cladding material, wherein the reflective index of the core is higher than the reflective index of the cladding, such that the infrared light experiences total internal reflection when passing through the one or more light guides.

20. The intra-oral scanning system of claim 18, wherein the one or more light guides comprise one or more mirrors such that the infrared light experiences total internal reflection when passing through the one or more light guides.

21. The intra-oral scanning system of claim 18, further comprising one or more windows between the infrared light source and the one or more light guides.

22. The intra-oral scanning system of claim 21, wherein the one or more windows are made from polymers and/or glass.

23. The intra-oral scanning system of claim 21, further comprising a first window and a second window, the first and second windows configured to couple the infrared light from the infrared light source to the one or more light guides.

24. The intra-oral scanning system of claim 23, wherein air gaps between the infrared adapter and the first window are filled with a transparent cladding material.

25. The intra-oral scanning system of claim 11, wherein the infrared adapter is configured to attach to the scanning tip by snapping and/or sliding onto the scanning-tip.

26. The intra-oral scanning system of claim 1, wherein the scanning tip further comprises a recognition-interface linked to an integrated memory located in the scanning-tip, the recognition-interface being configured to be read by a recognition-component located on the scanning device.

27. The intra-oral scanning system of claim 1, wherein the scanning tip comprises a tubular member comprising:

a distal end comprising a first optical opening configured to transmit the at least white light to the teeth, and a proximal end comprising a second optical opening configured to transmit the at least white light from the scanning device to the first optical opening, and the proximal end further comprising a mounting interface configured to mount the scanning tip to the scanning device.

28. The intra-oral scanning system of claim 1, wherein the scanning tip comprises a shell made of at least two separate parts.

* * * * *